US009612233B2

(12) United States Patent
Bristow

(10) Patent No.: US 9,612,233 B2
(45) Date of Patent: *Apr. 4, 2017

(54) THERAPEUTIC USE FOR ALPHA1 PROTEINASE INHIBITOR IN HEMATOPOIESIS

(75) Inventor: Cynthia L. Bristow, New York, NY (US)

(73) Assignees: The Institute for Human Genetics and Biochemistry, New York, NY (US); Cynthia L. Bristow, Long Beach, NY (US)

( * ) Notice: Subject to any disclaimer, the term of this patent is extended or adjusted under 35 U.S.C. 154(b) by 521 days.

This patent is subject to a terminal disclaimer.

(21) Appl. No.: 13/302,821

(22) Filed: Nov. 22, 2011

(65) Prior Publication Data

US 2012/0172286 A1 Jul. 5, 2012

Related U.S. Application Data

(63) Continuation of application No. 11/566,903, filed on Dec. 5, 2006, now abandoned.

(60) Provisional application No. 60/748,137, filed on Dec. 6, 2005.

(51) Int. Cl.
| | |
|---|---|
| *A61K 38/04* | (2006.01) |
| *A61K 38/48* | (2006.01) |
| *A61K 38/16* | (2006.01) |
| *G01N 33/50* | (2006.01) |

(52) U.S. Cl.
CPC ..... *G01N 33/5047* (2013.01); *G01N 2333/95* (2013.01); *G01N 2800/52* (2013.01)

(58) Field of Classification Search
None
See application file for complete search history.

(56) References Cited

U.S. PATENT DOCUMENTS

| 5,166,134 A | 11/1992 | Lezdey et al. |
| 6,129,911 A | 10/2000 | Faris |
| 6,849,605 B1 * | 2/2005 | Shapiro .................. 514/3.8 |
| 2002/0004477 A1 | 1/2002 | Bristow |
| 2003/0022249 A1 | 1/2003 | Schmitz et al. |

OTHER PUBLICATIONS

Bristow, 2012, PLosone, vol. 7, issue 2, e31383, pp. 1-10.*
Mofenson, 1997, the Journal of Infectious Diseases, vol. 175, pp. 1029-1038.*
Shapiro, 2001, FASEB J, vol. 15, pp. 115-122.*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Bowie et al. (Science, 1990, 247:1306-1310).*

Ali, HI, Tomhave, E.D., Richardson, R.M., Haribabu, B., and Snyderman, R. (1996). Thrombin primes responsiveness of selective chemoattractant receptors at a sige distal to G protein activation. J. Bio. Chem. 271, 3200-3206.
Banda, M.J., Rice, A.G., Griffin, G.L., and Senior, R.M. (1988). a1 proteinase inhibitor is a neutrophil chemoattractant after proteolytic inactivation by macrophage elastase. J. Biol. Chem. 263, 4481-4484.
Barbey-Morel, C. and Pertmutter, D.H. (1991). Effect of Pseudomonas elastase on human nomonuclear phagocyte a1-antitrypsin expression. Pediatr. Res 29, 133-139.
Beck, J.D., Eke, P., Lin, D., Madianos, P., Couper, D., Moss, K., Elter, J., Heiss, G., and Offenbacher, S. (2005). Associations between 1gG antibody to oral organixms and carotid intima-medial thickness in community-dwelling adults. Atherosclerosis 183, 342-348.
Benson, K.F., Li, F.Q., Person, R.E., Albani, D., Duan, Z., Wechsler, J., Meade-White, K., Williams, K., Acland, G.M., Niemeyer, G., Lothrop, C.D., and Horwitz, M. (2003). Mutations associated with neutropenia in dogs and humans disrupt intracellular transport of neutrophil elastase. Nat. Genet 35, 90-96.
Berninger, R.W., (1985). Alpha 1-antitrypsin. J. Med. 16, 23-99.
Bjorkman, P.J., Saper, M.A., Samraoui, B., Bennett, W.S., Strominger, J.L., and Wiley, D.C. (1987). Structure of the human class 1 histocompatibility antigen, HLA-A2. Nature 329, 506-512.
Brantly, M.L., Wittes, J.T., Vogelmeier, C.F., Hubbard, R.C., Fells, G.A. and Crystal, R.G. (1991). Use of a highly purified alpha 1-antitrypsin standard to establish ranges for the common normal and deficient alpha 1-antitrypsin phenotypes. Chest 100, 703-708.
Bristow, C.L. (2001). Slow human innumodeficiency virus (HIV) infectivity correlated with low HIV coreceptor levels. Clin. Diagn. Lab. Immunol. 8, 932-936.
Bristow, C.L., di Meo, F., and Arnold, R.R. (1998). Specific activity of a1 proteinase inhibitor and a2 macroglobulin in human serum. Application to insulin-dependent diabetes mellitus. Clin. Immunol. Immunopathol. 89, 247-259.

(Continued)

*Primary Examiner* — Brian J Gangle
*Assistant Examiner* — Andrea McCollum
(74) *Attorney, Agent, or Firm* — Fish & Richardson P.C.

(57) ABSTRACT

A previously unrecognized fundamental property of $\alpha_1$Proteinase Inhibitor ($\alpha_1$PI) is to regulate the phenotypic composition of circulating and tissue-associated cells derived from hematopoietic stem cells. The present invention comprises screening for various unmodified and modified $\alpha_1$PI's which are useful in the treatment of abnormalities in the number of cells of myeloid or lymphoid lineage that are associated with HIV-1 infection, microbial infection, leukemia, solid tumor cancers, atherosclerosis, autoimmunity, stem cell transplantation, organ transplantation, and other diseases affected by cells of the immune system. The interaction of $\alpha_1$PI with its receptors, Human Leukocyte Elastase Cell Surface ($HLE_{CS}$) and Low Density Lipoprotein-Receptor Related Protein (LRP), influences the level of cells of different lineages. Genetic and proteolytic modification of $\alpha_1$PI is used to target these receptors to increase or decrease specific cell populations, as needed, in the various disease states.

8 Claims, 4 Drawing Sheets

(56) References Cited

OTHER PUBLICATIONS

Bristow,C.L., Fiscus.S.A., Flood,P.M., and Amold,RR (1995). Inhibition of HIV-I by modification of a host membrane Drotease, Int. Immune!. 7, 239~249.

Bristow,C.L Mercatante,D.R., and Kale,R. (2003). HIVw1 preferentially binds receptors co~patched with cell surtace elastase. Blood 102, 4479-4486.

Bristow,C.L., Patel,H., and Arnold.RR (2001). Self antigen prognostic for human immunodeficiency virus disease proQression, Clin Diagn. Lab. Immunol. 8,937-942.

Brodala,N., Merricks,E.P., Bellinger,D.A., Damrongsri,D., Offenbacher,S., Beck,J., Madianos,P., Sotres,D., Chang,Y.L., Koch,G., and Nichols.T.C. (2005). Porphyromonas gingivalis Bacteremia Induces Coronary and Aortic Atherosclerosis in Normocholesterolemic and HVDercholesterolemic PiQs. Arterioscler Thromb Vasc Bioi 25, 1446~1451.

Cantin,AM. and Waods,D.E. (1999). Aerosolized Prolastin Suppresses Bacterial Proliferation in a Model of Chronic Pseudomonas aeruginosa Lung Infection. American Journal of Respiratory and Critical Care Medicine 160, 1130~1135.

Castro,K.G., Ward,JW., Slutsker.I., Buehler,J'w., Jaffe.Jr.J'w., Berkelman,R.I., and Curran,J.W. (1992).1993 revised classification system for HIV infection and expanded surveillance case definition for AIDS among adolescents and adults. Morbid, Mortal. Weekly Rep. 41, 1-19.

Cepinskas,G., Sandig,M., and KVietys,P.R (1999). PAF-Induced elastase-dependent neutrophil transendothelial migration is associated with the mobilization of elastase to the neutrophil surface and localization to the migrating front. J. Cell Science 112, 1937-1945.

Chowanadisai,W., Huang,J., Huang,N., and Lonnerdal,B. (2003). Stability of recombinant human alpha 1-antitrypsin produced in rice in infant formula. J Nutr Biochem 14, 386-393.

Cottler-Fox,M.H., Lapidol,T., Petit,I., Kollet,O., DiPersio,J.F., Unk,D., and Devine,S. (2003). Stem Cell Mobilization. HematoloQY 2003, 419-437.

Courtney,M., Buchwalder,A., Tessier,L.-H.J.M., Benavente,A., Balland,A., Kohli,V., Lathe,R, Tolstoshev.P., and Lecocq,J.P. (1984). High-level production of biologically active human alpha I-antitrypsin in *Escherichia coli*. Proc Natl Acad Sci USA 81, 669-673.

Csernok,E., Ludemann,J., Gross,W.L., and Bainton,D.F. (1990). Ultrastructural localization of proteinase 3, the target antigen of anti-cytoplasmic antibodies circulating in Wegener's granulomatosis. Am. J. Pathol. 137, t 113-1120.

Current Protocols in Molecular Biology (2002). Greene Publishing Associates and Wiley-Intersciences, New Yorkt, (8.5.1-8.5.10).

Cygler,M., Rose,D.R., and Bundle,D.R. (1991). Recognition of a cell-surface oligosaccharide of pathogenic *Salmonella* by an antibody Fab fragment. Science 253, 442-445.

Desrochers,P.E .. Mookhtiar,K., Van Wart,H.E., Hasty,K.A., and Weiss,S.J. (1992). Proteolytic inactivation of alpha 1-proteinase inhibitor and alpha 1-antichymotrypsin by oxidatively activated human neutrophil metalloproteinases. Journal of Biological Chemistry 267, 5005-5012.

Dichtl,W. Moraga,F., Ares,M.P.S., Crisby,M., Nilsson,J., Lindgren,S., and Janciauskiene,S. (2000). The Carbox~-Tenminal Fragment of [alpha]1 -Antitrypsin Is Present in Atherosclerollc Plaques and Regulates Inflammatory Transcription Factors in Primary Human Monocytes. Molecular Cell Bioloav Research Communications 4, 50~61.

Elliott.P.R., Pei,X.Y., Dafforn,T.R., and Lomas,DA (2000). Topography of a 2.0 A structure of alpha1-antitrypsin reveals targets for rational drug design to prevent conformational disease In Process Citationl. Protein Sci 9,1274-1281.

Flotte,T.R., Br~~tIY,~.'I., Spencer,L.T., Byrne,B.J., Spencer,C.T., Baker,D.J., and Humphries,M. 2004. Phase I trial of Intramuscular injection of a recombinant adeno-associated virus alpha 1 antitrypsin (rAAV2-CB-hAAT) gene vector to AAT-deficient adults. Hum Gene Ther 15, 93-128.

Grazladel,I., Gaggl,S., Kaserbacher,R Braunstelner,H and Vogel,W. (1994). The acutephase protein alpha 1•antitrypsln inhibits growth and proliferation of human early erythroid progenitor cells (bur5t~forming units-erythroid) and of human erythroleukemic cells (K562) in vitro by interferina with transferrin iron uptake. Blood 83, 260-268.

Gullberg,U., Lindmar1<,A., Lindgren.G., Persson,A.-M., Nllsson,E., and Olsson, I. (1995). Carboxylwterminal prodomaln-deleted human leukocyte elastase and cathepsin G are efficiently targeted to granules and enzymatically activated in the rat basophilic/mast cell line RBL. J.Bio. Chem. 270, 12912-12918.

Horwitz,M., Benson,K.F., Duan,Z., Li,F.Q., and Person,RE. (2004). Hereditary neutropenia: dogs explain human neutrophil elastase mutations. Trends Mol. Med, 10, 163-170.

Horwitz,M Benson.K.F., Person,RE., Aprlkyan,A.G., and Dale,D.C. (1999). Mutations In ELA2, encoding neutrophil elastase, define a 21-day clock in cyclic haematopoiesis. Nat. Genet. 23, 433436.

Janciauskiene,S. and Lindgren,S. (1999). Effects of fibrillar C-terminal fragment of cleaved alpha1-antitrvpsln on cholesterol homeostasis in HepG2 cells. Hepatology 29. 434-442.

Jansen,J., Hanks,S., Thompson,J.M., Dugan,M.J., and Akar,L.P. (2005). Transplantation of hematopoietic stem cells from the oerloheral blood. J Cell Mol Med. 9, 37-50.

Jean,F., Stella,K., Thomas,L., Lul,G., Xlang,Y., and Reason,A.J. (1998). alpha 1-antitrypsin Portland, a bioengineered serpin highly selective for turin: Application as an antipathogenic apent. Proc Natl Acad Sci USA 95, 7293-7298.

Joslin,G., Fallon.RJ Bullock,J., Adams,S.P., and Perlmutter.D.H. (1991). The SEC receptor recognizes a pentapeptide neodomain of alpha-1 antitrypsin-protease, J. Biol. Chem. 266, 11282-11288.

Klndzelskii,AL. and Petty,H.R. (2003). Intracellular Calcium Waves Accompany Neutrophil Polarization, Formylmethionyl-leucylphenylalanlne Stimulation, and Phagocytosis: A High Speed Microscopy Study. J. Immunol. 170,64-72.

Klrschfink,M. (2002). CI-Inhibitor and transplantation. Immunolobiology 205, 534•541.

Kounnas,M.Z., Church,F.C., Argraves,W.S., and Strlckland,D.K. (1996). Cellular internalization and degradation of antithrombin III-thrombin, heparin cofactor II-thrombin, and alpha 1-antitrypsin-trypsin complexes is mediated by the low density lipoprotein receptor-related protein. J. Biol. Chem. 271, 6523-6529.

Lapidot,T. and Petit,I. (2002). Current understanding of stem cell mobilization: The roles of chemokines, proteolytic enzymes, adhesion molecules, cytokines, and stromal cells. Exp. Hematol. 30, 973-981.

Leonard,C.K .. Spellman,M.W., Riddle,L., Harris,R.J., Thomas,J. N., and Gregory,T.J. (t987). Assignment of intrachain disulfide bonds and characterization of potential glycosylation. J. Biol. Chem. 265,10373-10362.

Li,W Savinov,A.Y., Rozanov,O.v., Golubkov,V.S., Hedayat,H., Postnova,T.I., Golubkova,N.V., L1nli,Y., Krajewski,S., and Strongin,A.Y. (2004). Matrix Metalloproteinase-26 Is Associated with Estrogen-Dependent Malignancies and Targets {alpha}1-Antitrypsin Serpin. Cancer Res 64, 6657-6665.

Luisetti,M. and Travis,J. (1996). Bioengineering: alpha 1-antiproteinase Inhibitor site-specific mutagenesis. The prospect for improving the inhibition. Chest 110, 278-263.

Marinaki,S., Neumann,!., Kalsch,A.I., Grimminger,P., Breedijk,A., Birck,R., Schmitt,W., Waldherr,R, Yard,BA, and van der Woude,F.J. (2005). Abnormalities of CD4+ T cell subpopulations in ANCA-associated vasculitls. Clinical and Experimental Immunology 140, 161-191.

Mast,A.E., Enghild,J.J., Nagase,H., Suzuki,K., Pizzo,S.V., and Salvesen,G. (1991). Kinetics and physiologic relevance of the inactivation of alpha 1-proteinase inhibitor, alpha 1-antichymotrypsin, and antithrombin III by matrix metalloproteinases-1 (tissue collagenase),-2 (72-kDa gelatinaseltype IV collagenase), and -3 (stromelysin). Journal 01 Biological Chemistry 266,15610-15616.

Mellet,P., Boudier,C., Mely,Y., and Bieth,J.G. (1996). Stopped Flow Fluorescence Energy Transfer Measurement of the Rate Constants Describing the Reversible Formation and the Irreversible Rear-

(56) References Cited

OTHER PUBLICATIONS rangement of the Elastase-alpha 1-Proteinase Inhibitor Complex, Journal of Biolooical Chemistry 273, 9119-9123.
Messmer,D., Jacque,J.-M., Santisteban,C., Bristow,C.L., Han,S.-Y., Villamide-Herrera,L., Mehlhop,E.R, Marx,PA, Slelnman,R.M., Gettie,A., and Pope,M. (2002). Endogenously expressed nef uncouples cytokine and chemokine production from membrane phenotypic maturation in dendritic cells. J. Immunol. 169,4172-4182.
Moore,J.P., Sattentau,Q.E., Wyatt,R., and Sodroski,J. (1994). Probing the slructure 01 the human immunodeficiency virus surface glycoprotein gp120 with a panel of monoclonal antibodies. J. Viral. 68,469-484.
Nenari,M., Berthet,V., Rigot,V., Laforest,S., Jacquier,M.F., Seidah,N.G., Remy,L., Bruyneel,E., Scoazec,J.Y Marvaldi,J., and Luis,J. (2004), Inhibition of Praprotein Convertases Enhances Cell Migration and Metastases Development of Human Colon Carcinoma Cells in a Rat Model. Am J Pathol 164, 1925-1933.
Nukiwa,T., Satoh,K., BrantlY,M,L., Ogushi,F., Fells,G.A., Courtney,M., and Cryslal,RG. (1986). Identification of a second mutation in the protein-coding sequence of the Z type alpha 1-antitrypsin gene. J. Biol. Chern. 261, 15989-15994.
Pa!ucka,A.K., Ohodapkar,M.V., Paczesny,S., Ueno,H., Fay,J., and Banchereau,J. (2005). Boosting Vaccinations with peptide-pulsed C034+ progenitor-derived dendritic cells can.expand long-lived melanoma peptide-specific CDB+ T cells in patients with metastatic melanoma. J Immunother. 28, 158-168.
Parfrey,H., Mahadeva,R., Ravenhill,N.A., Zhou,A., Oaffom,T.R., Foreman,RC., and Lomas,D.A. (2003). Targeting a surface cavity of alpha 1 antltrypsin to prevent conformational disease. J. Biol.Chem. 278 33060-33066.
Pei,D., Majmudar,G., and Weiss,S.J. (1994). Hydrolytic inactivation of a breast carcinoma cell-derived serpin by human stromelvsin-3. J. Biol. Chem. 269, 25849-25855.
Pendergraft,W.F., Preston,G.A., Shah,RR., Tropsha,A Carter,C.W Jennette,J.C., and Falk,RJ. (2003). Autoimmunity is triggered by cPR-3(105-201), a protein complementary to human autoantigen protelnase-3. Nat Med. 10 Epub Dec. 7, 2003, 72-79.
Percherancier,Y., Berchiche,Y Slight,!., Volkmer-Engert,R., Tamamura,H., Fujii,N., Bouvier,M., and Heveker,N. (2005). Bioluminescence resonance energy transfer reveals ligand-induced conformational changes in CXCR4 homo- and heterodimers. Journal of Biological Chemist, M411151200.
Perkins,S.J., Smith,K.F Nealis,A.S., Haris,P,I Chapman, D., Bauer,C.J and Harrison,RA, (1992). Secondary structure changes stabilize the reactive-centre cleaved form of SERPINs. J. Mol. Biol. 228 1235-1254.
Person,RE., Li,F,-Q., Duan,Z., Benson,K.F., Wechsler,J., Papadaki,H.A., Eliopoulos,G.,.Kaufman,C Bertolone,S.J., Nakamoto,B Papayannopoulou,T., Grimes,H.I., and Horwitz,M, (2003). Mutations in proto—oncogene GFI1 cause human neutropenia and target ELA2, Nature Genetics 34, 308-312.
Petit,I., Szyper-Kravitz,M., Nagler,A., Iahav,M .. Peled,A .. Habler,I .. Ponomaryov,T.. Taichman,R.S., Arenzana~Seisdedos,F Fujii,N., Sandbank,J., Zipori,D., and Lapldot,T. (2002). G-CSF induces stem cell mobilization by decreasing bone marrow SDF-1 and up-regulating CXCR4. Nature Immunol 3, 687-694.
Poller,W., Willnow,T.E., Hilperi,J., and Herz,J. (1995). Differential recognition of alpha 1-antitrypsin~elastase and alpha 1-antichymotrypsin-cathepsin-G complexes by the low density lipoprotein receptor-related protein. J. Biol. Chem. 270, 2841-2845.
Pratt,C.w., Roche,P.A., and Pizzo,S.V. (1987). The role of inter-a-trypsin inhibitor and other proteinase inhibitors in the plasma clearance of neutrophil elastase and plasmin. Arch. Biochem. Biophvs. 258, 591-599.
Ratner,I .. Haseltine,W., Patarca,R, Livak,K.J .. Stareich,B., Joseph,S.F., Doran,E.R, Rafalski,J.A,. Whitehom,E,A., Baumeister,K., and et al. (1985). Complete nucleotide sequence of the AIDS virus, HTIV-IIL Nature 313, 277-284.

Rooney,C.P., Taggart,C .. Coakley,R, McElvaney,N.G., and O'Neill,S.J. (2001). Anti-Proteinase 3 Antibody Activation of Neutrophils Can Be Inhibited by alpha 1~Antitrypsin. American Journal of Respiratory Cell and Molecular BioloDV 24, 747-754.
Rutjens,E.B.~J:S., Verschoor,E., Bogers,W., Koopman,G., and HeeneY,J, (2003). Lentivirus infections and mechanisms of disease resistance in chimpanzees. Front. Biosci. 8, d1134-1145.
Sandler,M., Gemperli,B,M Hanekom,C and Kuhn,S.H. (1988), Serum a1~protase inhibitor in diabetes mellitus: reduced concentration and impaired activity, Diabetes Res Clin Pract 5, 249-255.
Sandoval,C .. Stojanova,A., DiFalco,M.R., and Congote,L.F. (2003). The fusion of IGF I with stromal cell-derived factor I or (alpha]1 proteinase inhibitor alters their mitogenic or chemotactic activities while keeping their ability to inhibit HIV~1~gp120 binding. Biochemical Pharmacology 65, 2055-2063.
Schuler, G., Schuler~Thurner,B and Steinman,R.M. (2003). The use of dendritic cells in cancer immunotherapy. Current Opinion in Immunology 15, 138~147.
Sifers,RN., Brashears-Macatee,S., Kidd,V.J., Muensch,H and Woo,S.I. (1988). A frameshift mutation results in a truncated alpha 1~antitrypsin that is retained within the rough endonlasmic reticulum. Journal of Bioloogical Chemist 263, 7330-7335.
Sinico,RA, Radice,A.N.T,O., kehata,M.A.S.A, iammerresi,G,AI.A, orace,C,AT.E., rrigo,G.I.R.O .. ollini,B.R.U.N., Vecchi,M.A.U.R., and Iacomini,J. (2005). Anti-C1q Autoantibodies in Lupus Nephritis: Prevalence and Clinical Significance, Ann NY Acad Sci 1050, 193-200.
Rosenberg, et al, 1984, "Synthesis in Yeast of a Functional Oxidation-Resistant Mutant of Human ALPHA1 Antitrypsin", Nature-312: 77-80.
Stefansson, et al, 2004, "Mutants of Plasminogen Activator Inhibitor-1 Designed to Inhibit Neutrophil Elastase and Cathepsin G Are More Effective In Vivo Than Their Endogenous Inhibitors", The Journal of Biological Chemistr 279(29): 29981-29887.
George,.et al, 1984, "A Genetically Engineered Mutant of Alpha 1-Antitrypsin Protects.Connective Tissue From Neutrophil Damage and May Be Useful in Lung Disease", The Lancet 324: 1426 • 142B.
Song,G., Goudy,K., Campbell-Thompson,M., Wasserfall,C., Scott-Jorgensen,M., Wang,J .. Tang,Q .. Crawford,J.M., Ellis,T.M., Atkinson,M.A., and Flolle,T.R. (2004). Recombinant adeno-associated virus-mediated alpha-1 antitrypsin gene therapy prevents type I diabetes in NOD mice. Gene Ther 11,181-186.
Talmud,P.J., Martin,S .. Steiner,G .. Flavell,D.M., Whitehouse,D.B., Nagl,S., Jackson,R., Taskinen,M.R., Frick,M.H., Niemlnen,M.S., Kesaniemi,Y.A., Pastemack,A., Humphries,S.E Syvanne,M., and the Diabetes Atherosclerosis Intervention Study Investigators (2003). Progression of Atherosclerosis Is Associated With Variation in the {alpha}1-Antitrypsin Gene. Arterioscler Thromb Vasc Bioi 23, 644-649.
Tavor.S., Pelit,I., Porozov;S., Goichberg,P., Avigdor,A., Sagiv,S., Nagler,A., Naparslek,E., and Lapidot,T. (2005). Motility, proliferation and egress to the Circulation of human AML cells in transolanted NOD/SCID mice are elastase dependent. Blood 106, 2120-2127.
Terashima,M., Murai,T., Kawamura,M., Nakanishi,S., Stoltz,T., Chen,L., Drohan,W., Rodriguez,R.L., and Katoh,S. (1999). Production of functional human a.1-antitrypsin by plant cell culture. Apol Microbiol Biotechnol 52, 516-523.
Virella,G., Wohltmann,H., Sagel,J., Lopes-Virella,M.F.L Kilpatrick,M .. Phillips,C.B., and Colwell,J. (1981). Soluble immune complexes in patients with Diabetes Mellitus: Detection and patholoogical significance. Diabetologia 21, 184-191.
Weaver,A.M., Hussaini,I.M., Mazar,A., Henkin,J., and Gonias,S.L. (1997), Embryonic Fibroblasts That Are Genetically Deficient in Low Density Lipoprotein Receptor-related Protein Demonstrate Increased Activity of the Urokinase Receptor System and Accelerated Migration on Vitronectin. Journal of BioloQical Chemistry 272, 14372-14379.
Wei,X., Decker,J.M., Wang,S., Hui,H .• Kappes,J,C., Wu,X., Salazar-Gonzalez,J.F., Salazar,M.G., KilbY,J.M., Saag,M.S., Komarova,N.L., Nowak,M.A., Hahn,B.H., Kwong,P.D., and Shaw,G.M. [20031. Antibody neutralization and escape by HIV-1. Nature 422,307-312.

(56) References Cited

OTHER PUBLICATIONS

Winkler,I.G., Hendy,J., Coughlin,P., Horvath,A., and Levesque,J.P. (2005). Serine protease inhibitors serpina1 and serpina3 are down-regulated in bone marrow during hematopoietic Progenitor mobilization. The Journal of Experimental Medicine 201, 1077-1088.

Wolf,K., Muller,R., Borgmann,S Brocker,E,B and Fnedl,p. (2003). Amoeboid shape change and contact guidance: T-lymphocyte crawling through fibrilar collagen Is independent of matrix remodeling by MMPs and other proteases. Blood 102, 3262-3269.

Wright,S.D. and Meyer,B.C. (1986), Phorbol esters cause sequential activation and deactivation of complement receptors on polymorphonuclear leukocytes, J, Immunol. 136, 1759-1764.

Janciauskiene, S., at al., Human monocyte Activation by Cleaved form of Alpha-1-Antitrypsin Involvement of the Phagocytic Pathway: Eur. J. Biochem., vol. 265, 1999, PQ. 875-882.

Kingston, Robert E., "Chapter 9: Introduction of DNA into Mammalian Cells," Current Protocols in Molecular Biology, 2003, Supplement 64, p. 9.0.1-9.0.5.

Walsh, K.A., et al., "13] Serine Proteases," Ann. Rev. Biochem., vol. 29, No. 45,1960, p. 31-41.

Gabay, Cern, et al., MAcute-Phase Proteins and Other Systemic Responses to Inflammation, The New England Journal of Medicine, vol. 340, No. 6, Feb. 11, 1999, p. 448-454; 1.

Adeyemi, E.O., Hull, R.G., Chadwick, V.S., Hughes, G.R., and Hodgson, H.J. (1986). Circulating human leucocyte elastase in rheumatoid arthritis. Rheumatol. Int. 6, 57-6.

Garwicz,D., Lennartsson,A., Jacobsen,S.E.W. Guliberg,U., and Lindmark,A. (2005). Biosynthetic profiles of neutrophil serine proteases in a human bone marrow-derived cellular myeloid differentiation model. Haematolooica 90, 3844.

Girard,M., Mahoney,J., Wei,O., van der Ryst,E., Muchmore,E., Barre-Sinoussi,F., and Fultz,P.N, (1998), Genital infection affemale chimpanzees with human immunodeficiency virus-type 1. AIDS Res Hum Retroviruses 14, 1357•1367.

Janciauskiene,S., Wright,H.T., and Lindgren,S. (1999). Atherogenic properties of human monocytes induced by the carboxyl terminal proteolytic fragment of alpha1-antitrypsin. Atherosclerosis 147,263—275.

Jeppsson,J.O., Lilja,H., and Johansson,M. (1985). Isolation and characterlzalion of two minor fractions of alpha 1•antitrypsin by highwpertarmance liquid chromatographic chromatofocusing. J. Chromatoar 327. 173•177.

Hooper, N.M., (2002). Proteases: a Primer. Essays Biochem. 36, 1•8.

Mashiba,S" Wada,Y., Takeya,M., Sugiyama,A., Hamakubo,T., Nakamura,A" Noguchi,N., Niki,E., IumiiA., Kobayashi, M., Uchida,K., and Kodama,T. (2001). In Vivo Complex Formation of Oxidized (alpha)1-Anlitrypsin and LDL. Arterioscler Thromb Vase Biol 21, 1601-1606.

* cited by examiner

SEQUENCE LISTING

```
<160> NUMBER OF SEQ ID NOS: 17

<210> SEQ ID NO 1
<211> LENGTH: 4
<212> TYPE: PRT
<213> ORGANISM: Human immunodeficiency virus

<400> SEQUENCE: 1

Tyr Lys Val Val
1

<210> SEQ ID NO 2
<211> LENGTH: 4
<212> TYPE: PRT
<213> ORGANISM: Homo sapiens

<400> SEQUENCE: 2

Gly Lys Val Val
1

<210> SEQ ID NO 3
<211> LENGTH: 417
<212> TYPE: PRT
<213> ORGANISM: Homo sapiens

<400> SEQUENCE: 3

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Tyr Arg Gln Leu
    50                  55                  60

Ala His Gln Ser Asn Ser Thr Asn Ile Phe Phe Ser Pro Val Ser Ile
65                  70                  75                  80

Ala Thr Ala Phe Ala Met Leu Ser Leu Gly Thr Lys Ala Asp Thr His
                85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
        115                 120                 125

Pro Asp Ser Gln Leu Gln Leu Thr Thr Gly Asn Gly Leu Phe Leu Ser
    130                 135                 140

Glu Gly Leu Lys Leu Val Asp Lys Phe Leu Glu Asp Val Lys Lys Leu
```

```
                145                 150                 155                 160
        Tyr His Ser Glu Ala Phe Thr Val Asn Phe Gly Asp Thr Glu Ala
                            165                 170                 175
        Lys Lys Gln Ile Asn Asp Tyr Val Glu Lys Gly Thr Gln Gly Lys Ile
                        180                 185                 190
        Val Asp Leu Val Lys Glu Leu Asp Arg Asp Thr Val Phe Ala Leu Val
                    195                 200                 205
        Asn Tyr Ile Phe Phe Lys Gly Lys Trp Glu Arg Pro Phe Glu Val Lys
                210                 215                 220
        Asp Thr Glu Glu Glu Asp Phe His Val Asp Gln Val Thr Thr Val Lys
        225                 230                 235                 240
        Val Pro Met Met Lys Arg Leu Gly Met Phe Asn Ile Gln His Cys Lys
                        245                 250                 255
        Lys Leu Ser Ser Trp Val Leu Leu Met Lys Tyr Leu Gly Asn Ala Thr
                    260                 265                 270
        Ala Ile Phe Phe Leu Pro Asp Glu Gly Lys Leu Gln His Leu Glu Asn
                275                 280                 285
        Glu Leu Thr His Asp Ile Ile Thr Lys Phe Leu Glu Asn Glu Asp Arg
            290                 295                 300
        Arg Ser Ala Ser Leu His Leu Pro Lys Leu Ser Ile Thr Gly Thr Tyr
        305                 310                 315                 320
        Asp Leu Lys Ser Val Leu Gly Gln Leu Gly Ile Thr Lys Val Phe Ser
                        325                 330                 335
        Asn Gly Ala Asp Leu Ser Gly Val Thr Glu Glu Ala Pro Leu Lys Leu
                    340                 345                 350
        Ser Lys Ala Val His Lys Ala Val Leu Thr Ile Asp Glu Lys Gly Thr
                355                 360                 365
        Glu Ala Ala Gly Ala Met Phe Leu Glu Ala Ile Pro Met Ser Ile Pro
            370                 375                 380
        Pro Glu Val Lys Phe Asn Lys Pro Phe Val Phe Leu Met Ile Glu Gln
        385                 390                 395                 400
        Asn Thr Lys Ser Pro Leu Phe Met Gly Lys Val Val Asn Pro Thr Gln
                        405                 410                 415
        Lys

<210> SEQ ID NO 4
<211> LENGTH: 38
<212> TYPE: PRT
<213> ORGANISM: Homo sapiens

<400> SEQUENCE: 4

Pro Met Ser Ile Pro Pro Glu Val Lys Phe Asn Lys Pro Phe Val Phe
1               5                   10                  15

Leu Met Ile Glu Gln Asn Thr Lys Ser Pro Leu Phe Met Gly Lys Val
            20                  25                  30

Val Asn Pro Thr Gln Lys
        35

<210> SEQ ID NO 5
<211> LENGTH: 5
<212> TYPE: PRT
<213> ORGANISM: Homo sapiens

<400> SEQUENCE: 5

Pro Met Ser Ile Pro
1               5
```

<210> SEQ ID NO 6
<211> LENGTH: 11
<212> TYPE: PRT
<213> ORGANISM: Homo sapiens

<400> SEQUENCE: 6

Ser Ile Pro Pro Glu Val Lys Phe Asn Lys Pro
1               5                   10

<210> SEQ ID NO 7
<211> LENGTH: 5
<212> TYPE: PRT
<213> ORGANISM: Homo sapiens

<400> SEQUENCE: 7

Phe Val Phe Leu Met
1               5

<210> SEQ ID NO 8
<211> LENGTH: 18
<212> TYPE: PRT
<213> ORGANISM: Homo sapiens

<400> SEQUENCE: 8

Phe Leu Met Ile Glu Gln Asn Thr Lys Ser Pro Leu Phe Met Gly Lys
1               5                   10                  15

Val Val

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggatcccc agggagatgc tgcccagaa                                    29

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcgctcgag ttatttttgg gtgggattca ccac                              34

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcttgacctg taactcgggc caggcgagct                                   30

<210> SEQ ID NO 12
<211> LENGTH: 30
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 12
cgcctagccc gagttacagg tcaagcagct                                         30

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctagaggatc ccatggacta caaggacgac gatgacaagg aa                           42

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gatcttcctt gtcatcgtcg tccttgtagt ccatgggatc ct                           42

<210> SEQ ID NO 15
<211> LENGTH: 20
<212> TYPE: PRT
<213> ORGANISM: Human immunodeficiency virus

<400> SEQUENCE: 15

Gly Gly Gly Asp Met Arg Asp Asn Trp Arg Ser Glu Leu Tyr Lys Tyr
1               5                   10                  15

Lys Val Val Lys
            20

<210> SEQ ID NO 16
<211> LENGTH: 21
<212> TYPE: PRT
<213> ORGANISM: Homo sapiens

<400> SEQUENCE: 16

Pro Phe Val Phe Leu Met Ile Asp Gln Asn Thr Lys Ser Pro Leu Phe
1               5                   10                  15

Met Gly Lys Val Val
            20

<210> SEQ ID NO 17
<211> LENGTH: 418
<212> TYPE: PRT
<213> ORGANISM: Homo sapiens

<400> SEQUENCE: 17

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

```
Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
            130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
            210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Gly Gly Met Ile Glu
385                 390                 395                 400

Gln Asn Thr Lys Ser Pro Leu Phe Val Gly Lys Val Val Asn Pro Thr
                405                 410                 415

Gln Lys
```

THERAPEUTIC USE FOR ALPHA1 PROTEINASE INHIBITOR IN HEMATOPOIESIS

This application claims priority under 35 U.S.C. §119(e) from Provisional Application No. 60/748,137 filed Dec. 6, 2005.

SEQUENCE LISTING

The instant application contains a Sequence Listing which has been submitted in ASCII format via EFS-Web and is hereby incorporated by reference in its entirety. Said ASCII copy, created on Feb. 15, 2012, is named 86519CON.txt and is 11,216 bytes in size.

BACKGROUND OF THE INVENTION

Full length active $\alpha_1$proteinase inhibitor ($\alpha_1$PI, $\alpha_1$antitripsin) is composed of 394 amino acids (aa) having a mass of approximately 55 kDa when fully glycosylated (Berninger, 1985). Hepatocytes are the primary source of $\alpha_1$PI, and in normal, healthy individuals, the range of circulating $\alpha_1$PI is 20-53 μM between the $5^{th}$ and $95^{th}$ percentiles (Brandy et al., 1991; Bristow et al., 1998). However, during the acute phase of the inflammatory response, $\alpha_1$PI may increase as much as 4-fold to 200 μM (Kushner, 1982). There are four common alleles of $\alpha_1$PI, and these are synthesized and secreted principally by hepatocytes (OMIM, 2000). However, there are more than a hundred genetic variants, some of which produce a molecule that prohibits secretion, and affected individuals manifest with 10-15% of the normal level of $\alpha_1$PI in blood (Benninger, 1985). Individuals with this inherited form of $\alpha_1$PI deficiency, especially males, are notably susceptible to respiratory infections and emphysema, and 80% who survive to adulthood succumb to respiratory failure between the fourth and sixth decades of life (Berninger, 1985). Prevalence is 0.03%, and $\alpha_1$PI augmentation therapy in affected individuals is the only approved therapeutic application of $\alpha_1$PI (OMIM, 2000).

Traditionally, $\alpha_1$PI has been characterized as a proteinase inhibitor which has highest affinity for soluble granule-released elastase ($HLE_G$). Evidence now suggests $\alpha_1$PI also interacts with cell surface HLE ($HLE_{CS}$) (Bristow et al., 2003; Tavor. S. et al., 2005). Both $HLE_{CS}$ and $HLE_G$ are synthesized and processed as a single molecular protein; however, HLE is targeted exclusively for the cell surface early in ontogeny and for granule compartmentalization later in ontogeny (Gullberg et al., 1995; Garwicz et al., 2005). Mutations in the HLE encoding gene that result in decreased HLE expression produce periodic cycling in hematopoiesis that affect monocytes in the opposite phase to neutrophils (Horwitz et al., 1999; Horwitz et al., 2004). Mutations that result in increased HLE produce twice fewer absolute numbers of circulating CD4+ and CD8+ lymphocytes, and 7 times more monocytic cells (Person et al., 2003).

The proteinases and proteinase inhibitors that govern cell motility and hematopoiesis have evolved a different functional pattern in mice from man, but there are many parallels. For example, in mice, it has been shown that high concentrations of HLE accumulate in bone marrow following granulocyte colony-stimulating factor (G-CSF) induced stem cell mobilization (Winkler et al., 2005). This accumulation was found to result from the down-regulation of $\alpha_1$PI expression. In man, the liver is the primary source of both $\alpha_1$PI and stem cells. As opposed to its function to inhibit the enzymatic activity of $HLE_G$, $\alpha_1$PI binding to $HLE_{CS}$ induces cell migration in a manner that does not appear to involve enzymatic activity (Wolf et al., 2003). The effect of $\alpha_1$PI on cell motility is especially profound during migration of stem cells and early progenitor cells. Hematopoiesis begins with stem cell migration from fetal liver through the periphery to the stromal area of hematopoietic tissue, retention, differentiation, and release of maturing progenitor cells back into the periphery. Migration of stem cells to, and myeloid-committed progenitor cells from bone marrow is controlled by $HLE_{CS}$, the chemokine stromal cell-derived factor-1 (SDF-1), and the SDF-1 receptor CXCR4 (Tavor. S. et al., 2005; Lapidot and Petit, 2002). Cell migration is dependent on the localization of $HLE_{CS}$ into podia formation at the leading edge of the cell (Tavor. S. et al., 2005; Cepinskas et al., 1999), and podia formation is induced by binding of active $\alpha_1$PI to $HLE_{CS}$ in a manner that includes co-localization of $HLE_{CS}$ with CD4 and CXCR4 (Bristow et al., 2003). The current method for therapeutic mobilization of myeloid-committed progenitor cells from bone marrow is by the action of G-CSF, and it has been shown that G-CSF mediates this activity by antagonizing CXCR4 and $HLE_{CS}$ (Lapidot and Petit, 2002). The molecular mechanisms that mobilize lymphoid-committed progenitors from hematopoietic tissue are not known. Evidence described in this application now suggests active $\alpha_1$PI mediates this activity (Examples 1-3 below). Following treatment with $\alpha_1$PI in animal models, the migration of transplanted human leukemia cells into circulation is decreased, but the migration of stem cells to hematopoietic tissue is increased (Tavor. S. et al., 2005). These results suggest that $\alpha_1$PI influences the migration of cells into and out of circulation depending, in part, on the stage of differentiation of the cell.

When bone marrow-derived erythroid progenitors cells (burst-forming units-erythroid) are incubated with $\alpha_1$PI in vitro, growth of immature cells is significantly suppressed (42.5%±5.5%) (Graziadei et al., 1994). In contrast, growth of mature cells is unaffected by $\alpha_1$PI (3.6%±3.4%). These results demonstrate that in addition to myeloid- and lymphoid-committed progenitors, $\alpha_1$PI influences the genesis of erythroid-committed progenitor cells dependent on their stage of differentiation.

Previous therapeutic application of $\alpha_1$PI has been restricted to augmentation in patients diagnosed with inherited $\alpha_1$PI deficiency for the purpose of ameliorating respiratory distress such as occurs in emphysema and chronic obstructive pulmonary disease (COPD). Considerable interest in producing recombinant $\alpha_1$PI has resulted in development of several successful expression systems including bacterial and plant cell expression as well as viral vector and oral delivery (Chowanadisai et al., 2003; Luisetti and Travis, 1996). Recombinant $\alpha_1$PI is in phase I clinical trials for augmentation in individuals with inherited $\alpha_1$PI deficiency (Flotte et al., 2004), and is in phase II clinical trials for treatment of atopic dermatitis. Recombinant $\alpha_1$PI has been tested for preventing the onset of type I diabetes in genetically predisposed mice (Song et al., 2004). Nevertheless, there is a need in the art for developing recombinant $\alpha_1$PI with due consideration of its conformation-dependent function to mobilize either lymphoid-lineage or myeloid-lineage maturing cells. As recognized by the inventor herein, because $\alpha_1$PI induces cell motility depending on its active or proteolytic ally modified conformation, various active and modified $\alpha_1$PI's provide powerful new therapeutics for mobilizing targeted cell subsets through tissue.

SUMMARY OF THE INVENTION

This invention is directed to the use of $\alpha_1$PI and modified $\alpha_1$PI to control the phenotypic composition of circulating and tissue-associated cells derived from hematopoietic stem cells. Various modified $\alpha_1$PI's are also provided. Screening methods and treatment for abnormalities in the phenotypic profile of blood cells are also provided. Such abnormalities are associated with, e.g., HIV-1 infection, microbial infection, leukemia, solid tumor cancers, atherosclerosis, autoimmunity, stem cell transplantation, organ transplantation, and other diseases affected by cells of the immune system. The invention is based, in part, on a previously unrecognized fundamental property of $\alpha_1$PI to regulate the phenotypic composition of circulating and tissue-associated cells derived from hematopoietic stem cells.

Accordingly, this invention provides a method for identifying a modified $\alpha_1$PI as suitable for use in treating a disease, disorder or condition in a subject, comprising: (a) producing the modified $\alpha_1$PI; and (b) measuring a biological activity of the modified $\alpha_1$PI in a biological assay for predicting effectiveness in treating the disease, disorder or condition in the subject, wherein the modified $\alpha_1$PI is identified as suitable for treating the disease, disorder or condition from a change in the biological activity relative to a control activity measured for a wild-type $\alpha_1$PI. In one embodiment, the modified $\alpha_1$PI is produced by site-directed mutagenesis, proteolysis, or both. In another embodiment, the disease, disorder or condition is selected from the group consisting of HIV-1 infection, bacterial infection, leukemia, a solid tumor, atherosclerosis, an autoimmune disease, organ transplantation, and stem cell transplantation. In another embodiment, the stem cell transplantation is autologous stem cell transplantation.

In another embodiment, the biological assay is selected from the group consisting of an elastase inhibition assay, a receptor co-capping assay, a cell motility assay, a lymphoid-committed progenitor cell mobilization assay, an HIV-1 gp120 antibody cross-reactivity assay, and an HIV-1 infectivity facilitation assay. In another embodiment, the subject is a human or a non-human animal. In another embodiment, proteolysis comprises contacting a wild-type or a recombinant $\alpha_1$PI with a protease selected from the group consisting of elastase, stromelysin-3, matrix metalloproteinase, collagenase, gelatinase, pepsin, plasmin, urokinase, chymotrypsin, thrombin, CD26, complement component C1, and complement component C3.

In another embodiment, site-directed mutagenesis comprises changing at least two wild-type amino acid residues selected from the group consisting of residues 370-374 and 385 to a non-wild-type residue, wherein one changed residue is at position 385. In another embodiment, at least one amino acid selected from the group consisting of residues 370-374 and 385 is changed from wild-type to glycine, threonine, or a hydrophobic amino acid. In another embodiment, the hydrophobic amino acid is selected from the group consisting of isoleucine, leucine, phenylalanine, tyrosine and valine.

This invention provides a modified human $\alpha_1$PI comprising a change in a wild-type amino acid residue selected from the group consisting of residues 370-374 and 385. In one embodiment, the genetically modified $\alpha_1$PI further comprises modification by proteolysis. In another embodiment, the wild-type amino acid residue is changed to glycine, threonine, or a hydrophobic amino acid. In another embodiment, the hydrophobic amino acid is selected from the group consisting of isoleucine, leucine, phenylalanine, tyrosine and valine. In another embodiment, the modified human $\alpha_1$PI comprises at least two changes in wild-type amino acid residues comprising a change at position 385 and a change at a position selected from the group consisting of positions 370-374. In another embodiment, the methionine at position 385 is changed to a non-methionine amino acid. In another embodiment, the non-methionine amino acid is selected from the group consisting of glycine, isoleucine, leucine, phenylalanine, threonine, and valine. In another embodiment, the modified human $\alpha_1$PI is capable of a reduced binding activity in an HIV-1 gp120 antibody cross-reactivity assay, relative to a wild-type $\alpha_1$PI. In another embodiment, the residue changes in the modified human $\alpha_1$PI comprise the following three amino acid substitutions: Phe372Gly; Leu373Gly; and Met 385Val. In another embodiment, the residue changes in the modified human $\alpha_1$PI consist of the following three amino acid substitutions: Phe372Gly; Leu373Gly; and Met 385Val.

This invention provides a method of treating a disease, disorder or condition in a subject in need of said treatment, comprising administering an effective amount of an unmodified or modified $\alpha_1$PI to the subject. In one embodiment, the modified $\alpha_1$PI is produced by site-directed mutagenesis, proteolysis, or both. In another embodiment, the disease, disorder or condition is selected from the group consisting of HIV-1 infection, bacterial infection, leukemia, a solid tumor, atherosclerosis, an autoimmune disease, organ transplantation, and stem cell transplantation. In another embodiment, the subject is a human or a non-human animal. In another embodiment, the modified $\alpha_1$PI comprises a change in a wild-type amino acid residue selected from the group consisting of residues 370-374, and further comprises a change in methionine at position 385. In another embodiment, methionine at position 385 is changed to a non-methionine amino acid selected from the group consisting of glycine, isoleucine, leucine, phenylalanine, threonine, and valine. In another embodiment, the modified $\alpha_1$PI is capable of a reduced binding activity in an HIV-1 gp120 antibody cross-reactivity assay, relative to a wild-type $\alpha_1$PI. In another embodiment, the amino acid changes in the modified $\alpha_1$PI comprise the following three amino acid substitutions: Phe372Gly; Leu373Gly; and Met 385Val. In another embodiment, the amino acid changes in the modified $\alpha_1$PI consist of the following three amino acid substitutions: Phe372Gly; Leu373Gly; and Met 385Val. In another embodiment, the treatment method further comprises administration of HIV-1 antiretroviral therapy. In another embodiment, the effective amount of modified $\alpha_1$PI is a dose equivalent to about 42 mg/kg of active wild-type $\alpha_1$PI.

This invention provides a method of treating a disease, disorder or condition in a subject in need of said treatment, comprising administering an effective amount of an active $\alpha_1$PI to the subject, wherein the disease, disorder or condition is selected from the group consisting of HIV-1 infection, bacterial infection, leukemia, a solid tumor, atherosclerosis, an autoimmune disease, organ transplantation, and stem cell transplantation. In one embodiment, the stem cell transplantation is autologous stem cell transplantation.

This invention provides a method of treating a disease, disorder or condition in a subject in need of said treatment, comprising administering an effective amount of an active $\alpha_1$PI to the subject, wherein the subject is characterized as having an abnormal or ineffective number of lymphocytes, monocytes, or dendritic cells.

This invention provides a method of treating a disease, disorder or condition in a subject in need of said treatment, comprising administering an effective amount of an inactive $\alpha_1$PI to the subject, wherein the disease, disorder or condition is selected from the group consisting of bacterial infection, neutropenia and immunosuppression.

This invention provides a method of treating a disease, disorder or condition in a subject in need of said treatment, comprising administering an effective amount of an inactive $\alpha_1$PI to the subject, wherein the subject is characterized as having an abnormal or ineffective number of granulocytes, monocytes, dendritic cells, eosinophils, or basophils. In one embodiment, the subject is a human or a non-human animal.

DETAILED DESCRIPTION OF THE INVENTION

Figure 1:
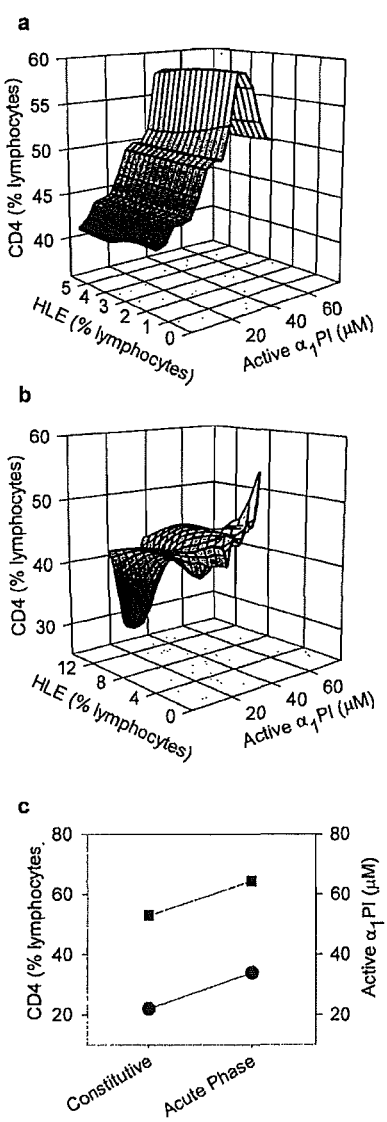
FIG. 1(a-c). Correlation of CD4 lymphocyte levels with active $\alpha_1$PI, $HLE_{CS}$ and SDF-1 in healthy individuals. (a) Increased active $\alpha_1$PI and decreased $HLE_{CS}^+$ lymphocytes predict increased CD4$^+$ lymphocytes in healthy subjects specifically selected to represent a wide spectrum of $\alpha_1$PI concentrations. CD4$^+$ lymphocytes (%)=50.48+0.27*active $\alpha_1$PI (μM)−2.67* $HLE_{CS}^+$ lymphocytes (%) ($r^2$=0.937, p<0.05, n=6). (b) Increased active $\alpha_1$PI and decreased $HLE_{CS}^+$ lymphocytes predict increased CD4$^+$ lymphocytes in healthy subjects representing the general population. CD4$^+$ lymphocytes (%)=37.80+0.43*active $\alpha_1$PI (μM)−1.56*$HLE_{CS}^+$ lymphocytes (%) ($r^2$=0.803, p<0.05, n=16). When SDF-1 is included in the model, CD4$^+$ lymphocytes (%)=44.46+0.54*active $\alpha_1$PI (μM)−1.65* $HLE_{CS}^+$ lymphocytes (%)−0.03* SDF-1 (pM) ($r^2$=0.875, p<0.05, n=16). (c) Active $\alpha_1$PI (■) and CD4$^+$ lymphocytes (●) increase proportionally during the acute phase of an enteric infection in a volunteer who was otherwise healthy.
Figure 2:
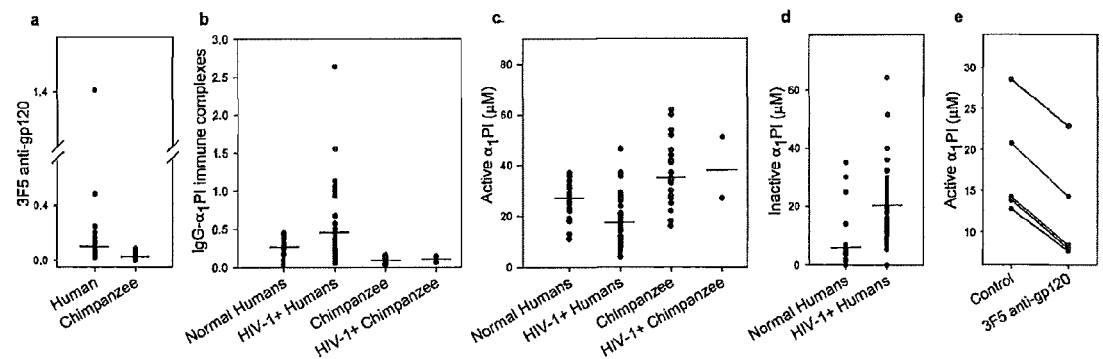
FIG. 2(a-e). Binding of anti-gp120 antibody to human, but not chimpanzee $\alpha_1$PI. (a) Monoclonal antibody 3F5 binding to $\alpha_1$PI in sera from 18 healthy humans and 20 healthy chimpanzees was measured in ELISA. Antibody bound ($A_{490\ nm}$) was normalized for the serum $\alpha_1$PI concentration in each specimen and is represented as $A_{490}$ nm/$\alpha_1$PI(μM). Binding of 3F5 was 8- to 14-fold greater to human than to chimpanzee $\alpha_1$PI (p<0.001). Measurements were repeated 6 times using 3F5 and once using monoclonal antibody 1C1. Representative measurements are depicted. Bars represent mean values. (b) The presence of IgG-$\alpha_1$PI immune complexes in sera ($A_{490\ nm}$) was detected in 11 of 38 HIV-1 infected patients, but not in sera from 9 healthy individuals, 20 healthy chimpanzees, nor in 2 chimpanzees 42 months following HIV-1 inoculation. Serum collected from healthy volunteers into tubes containing clot activating additive were excluded from immune complex analysis because of buffer incompatibility. Measurements were repeated at least 3 times, and representative data are depicted. Bars represent mean values. (c) Active $\alpha_1$PI concentration in HIV-1 infected patients (median 17 μM) was significantly below normal (median 26 μM, p<0.001). Active $\alpha_1$PI in sera from 20 healthy chimpanzees (median 35 μM) and 2 chimpanzees post-HIV-1 inoculation median (39 μM) was significantly greater (p<0.02) than from 18 human sera (median 26 μM). Active $\alpha_1$PI was measured in 8 serial dilutions of each serum sample. (d) Inactive $\alpha_1$PI concentration in HIV-1 infected patients (median 19 μM) was above normal (median 4 μM, p<0.001). (e) After incubating sera from 5 healthy individuals with monoclonal antibody 3F5, active $\alpha_1$PI (12±7 μM) was significantly lower than in control sera incubated with medium alone (18±7 μM, p<0.001). Bars represent mean values.
Figure 3:
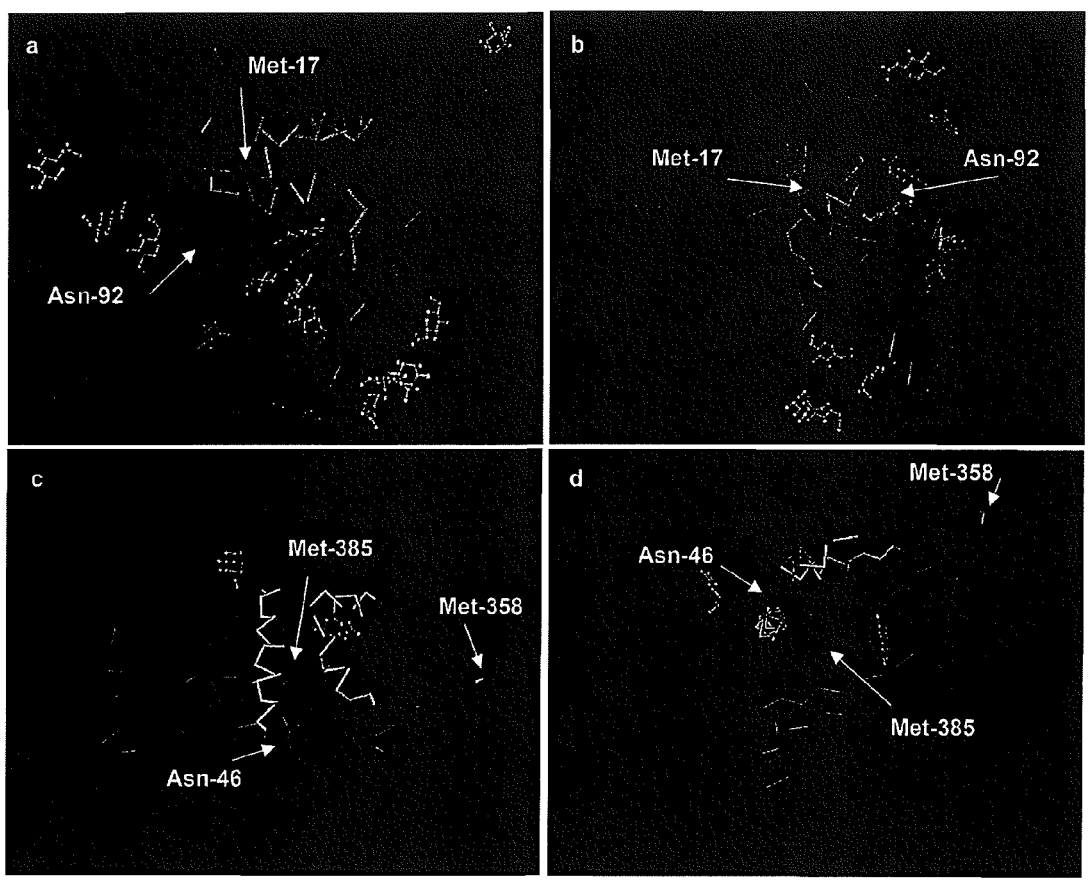
FIG. 3(a-d). Corresponding conformation at the 3F5-recognized domains in $\alpha_1$PI and CD4-complexed HIV-1 gp120. Structures for human $\alpha_1$PI (1HP7) and CD4-complexed HIV-1 gp120 (1RZJ) from the NCBI Molecular Modeling Database (MMDB) were analyzed using Cn3D software. Small carbohydrate structures were already associated with 1RZJ in MMDB, and the three associated with 1HP7 were added using Adobe Photoshop. HIV-1 gp120 is depicted from two perspectives (a,b) with two α-helices highlighted (aa 21-39 and 306-313). The gp120 peptide immunogen used to raise 1C1 and 3F5 (aa 300-321) is located at the C-terminus of gp120, and the linear segment YKVV (aa 315-318, SEQ ID NO: 1) along with the M-17 and the oligosaccharide-linked NGT (aa 92-94), are within 8A° of the conformational epitope. The gp120-homologous domain in $\alpha_1$PI is also located at the C-terminus of the protein, and is depicted from two perspectives (c,d) with the highlighted antiparallel β-sheet strand at the base of the cleft (aa 369-389), as well as the α-helices that form the mouth of the cleft (aa 28-44 and 259-277). M-385, which distinguishes human from chimpanzee $\alpha_1$PI, is indicated along with GKVV (aa 386-389, SEQ ID NO: 2), the oligosaccharide, and oligosaccharide-linked NST (aa 46-48). The proteinase reactive site M-358, is indicated for orientation.

Definitions:

Human $\alpha_1$PI—Alpha$_1$-Proteinase Inhibitor (Human) is a sterile, stable, lyophilized preparation of highly purified human alpha$_1$-proteinase inhibitor ($\alpha_1$PI) also known as alpha$_1$-antitrypsin derived from human plasma. There are three products of alpha$_1$-Proteinase Inhibitor (Human) that are currently FDA approved for treatment. Prolastin® produced by Talecris Biotherapeutics, Zemaira® produced by ZLB Behring, and Aralast™ produced by Baxter Healthcare Corp.

Active $\alpha_1$PI—the fraction of $\alpha_1$PI in plasma or other fluids that has the capacity to inhibit elastase activity.

Inactive $\alpha_1$PI—the fraction of $\alpha_1$PI in plasma or other fluids that does not have the capacity to inhibit elastase activity. Active $\alpha_1$PI may be inactivated by proteolytic cleavage, proteinase complexing, antibody complexing, or oxidation.

Genetically modified $\alpha_1$PI—active $\alpha_1$PI synthesized from the cDNA encoding human $\alpha_1$PI which has been modified by site-directed mutagenesis. There are no current recombinant products that have been FDA approved for treatment.

Proteolytically modified $\alpha_1$PI—active or genetically modified human $\alpha_1$PI which has been further modified by limited proteolysis to generate fragments. Proteolytic modification inactivates $\alpha_1$PI.

Pharmaceutical Composition—When formulated in a pharmaceutical composition, the therapeutic compound of the invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a statement government or listed in the U.S. Pharmacopeia or other generally recognized pharmacopeia for use in animals, and, more particularly, in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

1. Treatment population: Active $\alpha_1$PI promotes migration of lymphocytes and monocytic cells expressing $HLE_{CS}$ (Bristow et al., 2003) (Examples 1-3 below). Inactive $\alpha_1$PI promotes migration of neutrophils and cells expressing the LDL-receptor related protein, LRP (Kounnas et al., 1996; Weaver et al., 1997), Treatment with active human $\alpha_1$PI is indicated in individuals manifesting abnormal numbers of functional lymphocytes, monocytic cells, or dendritic cells such as in HIV-1 disease, stem cell transplantation, solid organ transplantation, autoimmune exacerbations, diabetes, leukemia, lymphoma, solid tumors, and, atherosclerosis. Treatment with inactive human $\alpha_1$PI is indicated in individuals manifesting abnormal numbers of functional granulocytic, monocytic cells, dendritic, eosinophilic, or basophilic cells such as in microbial infection, neutropenia, and immunosuppressed patients. Treatment outcome is determined as described below in Section 7 of the Detailed Description.

2. Treatment regimen: According to the Prolastin® Product Monograph, the Zemaira® prescribing information literature, and the Aralast™ prescribing information, the recommended dosage for $\alpha_1$PI is repeated weekly infusions of 60 mg/kg at a rate of 0.08 ml/kg/minute leading to the historical target threshold of 11 µM $\alpha_1$PI in serum. The ideal blood threshold is 34 µM $\alpha_1$PI, but this level has not been achieved therapeutically. Delivery is traditionally by infusion, but recombinant $\alpha_1$PI is also produced for ingestion (Chowanadisai et al., 2003).

The specific activity of Zemaira® is 70%, Prolastin® is 35%, and Aralast™ is 55% where specific activity is defined as inhibition of porcine pancreatic elastase (PPE) as described in the package insert. Thus, the recommended dose of Zemaira® $\alpha_1$PI may be stated as 42 mg/kg active $\alpha_1$PI, Prolastin® as 21 mg/kg, and Aralast™ as 33 mg/kg active $\alpha_1$PI. Conversely, the inactive fraction of Zemaira® is 30% or 18 mg/kg, of Prolastin® is 65% or 39 mg/kg, and of Aralast™ is 45% or 27 mg/kg The dosage of genetically modified $\alpha_1$PI is determined by its capacity to inhibit PPE as described in Section 6 of the Detailed Description (see also, U.S. Pat. No. 6,887,678). In accordance with the recommended treatment regimen using wild-type $\alpha_1$PI, subjects are infused with genetically modified $\alpha_1$PI at a dosage that is in the range of 1 to 420 mg/kg active $\alpha_1$PI, with a target blood threshold of 35 µM genetically modified $\alpha_1$PI. In some cases, either active or genetically modified $\alpha_1$PI are further modified by limited proteolytic cleavage to generate fragments that are chemotactic for myeloid-lineage cells. For example, in microbial infections that attend neutropenia, proteolytically modified $\alpha_1$PI is used to recruit neutrophils into infected tissue. In this case, individuals are infused with proteolytically modified $\alpha_1$PI at the concentration that is equivalent to 39 mg/kg inactive $\alpha_1$PI. In addition to being monitored for PPE inhibitory activity, proteolytically modified $\alpha_1$PI is screened as described in Section 3.2 of the Detailed Description for its capacity of to induce receptor capping and cell motility of myeloid-lineage blood cells such as neutrophils.

3. Recombinant $\alpha_1$PI: In addition to plasma-derived $\alpha_1$PI, recombinant $\alpha_1$PI has the capacity to mobilize progenitor cells. A bioengineered form of $\alpha_1$PI has been shown to partition into two cleavage fragments (Jean et al., 1998), and an $\alpha_1$PI-insulin-like growth factor chimera has been shown to induce chemotaxis (Sandoval et al., 2003). Modifications of recombinant $\alpha_1$PI provide an improvement specific to HIV-1 and other diseases for mobilization of specific progenitor cells.

3.1 Structural features of $\alpha_1$PI: The following represents the full length amino acid sequence for $\alpha_1$PI (accession # K01396) including the 24 aa signal peptide (SEQ ID NO: 3):

```
-24  MPSSVSWGIL  LLAGLCCLVP  VSLA

1  EDPQGDAAQK  TDTSHHDQDH  PTFNKITPNL  AEFAFSLYRQ  LAHQSNSTNI

51  FFSPVSIATA  FAMLSLGTKA  DTHDEILEGL  NFNLTEIPEA  QIHEGFQELL

101  RTLNQPDSQL  QLTTGNGLFL  SEGLKLVDKF  LEDVKKLYHS  EAFTVNFGDT

151  EEAKKQINDY  VEKGTQGKIV  DLVKELDRDT  VFALVNYIFF  KGKWERPFEV

201  KDTEEEDFHV  DQVTTVKVPM  MKRLGMFNIQ  HCKKLSSWVL  LMKYLGNATA

251  IFFLPDEGKL  QHLENELTHD  IITKFLENED  RRSASLHLPK  LSITGTYDLK

301  SVLGQLGITK  VFSNGADLSG  VTEEAPLKLS  KAVHKAVLTI  DEKGTEAAGA

351  MFLEAIPMSI  PPEVKFNKPF  VFLMIEQNTK  SPLFMGKVVN  PTQK
```

The known Asn-linked carboxylation sites (denoted in bold underlined letters) are found at aa 46, 83, and 247 (Nukiwa et al., 1986; Jeppsson et al., 1985). The oligosaccharide structure at each site is either tri-antenary or bi-antenary, and the various combinations give the protein a characteristic electrophoretic charge denoted as phenotypic subtypes of the four common genotypic alleles, M1A, M1V, M2, and M3.

The frequencies in, US Caucasians of M1A, M1V, M2, and M3 are 0.20-0.23, 0.44-0.49, 0.1-0.11, and 0.14-0.19, respectively, accounting for 95% of this population (Jeppsson et al., 1985). M1A is thought to be the oldest variant, and M1V has a single aa substitution, at position 213, Ala to Val. The M3 allele has a single aa difference with M1V, Glu to Asp at position 376. The M2 allele has a single aa difference with M3, Arg to His at position 101.

More than a hundred genotypic alleles have been identified, but except for the S and Z alleles, most of them are exceedingly rare (OMIM, 2000). The S allele, frequency 0.02-0.04, has a single aa substitution at position 264, Glu to Val, and individuals homozygous for this allele manifest 60% normal $\alpha_1$PI blood levels, but are not at risk for emphysema or other known diseases except in combination with the Z allele (Brantly et al., 1991; Sifers et al., 1988). The Z allele, frequency 0.01-0.02, has a single aa substitution at position 342, Glu to Lys, and individuals homozygous for this allele manifest 10% normal $\alpha_1$PI blood levels, and are at risk for emphysema and autoimmunity.

3.2 Functional properties of $\alpha_1$PI: There are three distinct activities of $\alpha_1$PI that are determined by sites in the C-terminal region of $\alpha_1$PI defined herein as aa 357-394 (SEQ ID NO: 4),

PMSI PPEVKFNKPF VFLMIEQNTK SPLFMGKVVN PTQK

The crystal structure for active $\alpha_1$PI (1HP7, NIH NCBI Molecular Modeling DataBase mmdbId:15959) is depicted in FIG. 3 with Met (aa 358) and Met (aa 385) designated. The β-sheet formation of the C-terminal region of $\alpha_1$PI (aa 369-394) is designated. Two α-helix domains (aa 27-44 and 257-280) shield the β-sheet domain in a manner resembling the antigen-binding cleft of the major histocompatibility complex.

The first activity of $\alpha_1$PI is its well characterized proteinase inhibition which is a property only of active, uncleaved $\alpha_1$PI. The reactive site for this activity is Met (aa 358) contained in the domain Pro-Met-Ser-Ile-Pro (PMSIP, aa 357-361, SEQ ID NO: 5). Active $\alpha_1$PI may be inactivated by proteinase complexing, cleavage, or oxidation of Met (aa 358). Interaction at the scissile bond Met-Ser (aa 358-359) may be mediated by many proteinases including $HLE_G$. The two cleavage products of $\alpha_1$PI may dissociate under some circumstances, but may remain associated in a new, rearranged configuration that may irreversibly incorporate $HLE_G$, but may not incorporate other proteinases, for example metalloproteinases (Perkins et al., 1992).

The tertiary structure for the rearranged $\alpha_1$PI configuration has not been solved (Mellet et al., 1998); however, X-ray diffraction and kinetic analyses of cleaved $\alpha_1$PI suggest that the strand SIPPEVKFNKP (aa 359-369, SEQ ID NO: 6) may separate 70A° from its original position and insert into the β-sheet formation on the opposite face of the molecule (β-sheet A) in a manner that would significantly alter proteinase and receptor recognition (Elliott et al., 2000). Thus, four configurations of the C-terminal region of $\alpha_1$PI are thought to occur (Table 1).

TABLE 1

Functions of the C-terminal region of $\alpha_1$PI

| | Proteinase Inhibition | Lymphoid cell migration | Myeloid cell migration | anti-gp120 binding | HIV-1 entry co-factor |
|---|---|---|---|---|---|
| Native configuration in the active $\alpha_1$PI | + | + | − | + | + |
| Rearranged configuration in cleaved $\alpha_1$PI | − | − | Unknown | + | − |
| Complexed with HLE in cleaved $\alpha_1$PI | − | − | + | Unknown | − |
| Independent of other $\alpha_1$PI cleavage products | − | Unknown | + | Unknown | Unknown |

Because the cleaved configuration of $\alpha_1$PI lacks proteinase inhibitory activity, in deficient concentrations of active $\alpha_1$PI, the result is emphysema and respiratory-related infections which are facilitated by the presence of certain environmental factors, cigarette smoke, microbial factors, and inherited mutations that prohibit successful production of active $\alpha_1$PI.

A second activity of $\alpha_1$PI is the stimulation of cell migration, and this activity is a property of both cleaved and uncleaved $\alpha_1$PI. Cleaved $\alpha_1$PI is recognized by LRP, and stimulates migration of myeloid-lineage cells including neutrophils and monocytic cells (Joslin et al., 1992). Active, uncleaved $\alpha_1$PI is recognized by $HLE_{CS}$ and stimulates migration of lymphoid-lineage cells and myeloid-committed progenitor cells (Bristow et al., 2003). Cell migration is initiated by $\alpha_1$PI-induced co-capping of receptors such as $HLE_{CS}$, CXCR4, and CD4 into podia formation (Cepinskas et al., 1999; Banda et al., 1988). In addition to the participation of podia formation during cell migration, this configuration is also the preferred binding site for HIV-1 (Bristow et al., 2003). The reactive site in $\alpha_1$PI for this activity is Phe-Val-Phe-Leu-M (FVFLM, aa 370-374, SEQ ID NO: 7).

A third non-physiologic activity of $\alpha_1$PI is binding to antibodies reactive with HIV-1 envelope protein gp120, and this activity results in inactivation of $\alpha_1$PI and blocking of the other two activities described above. The anti-gp120 monoclonal antibodies 1C1 (Repligen, Inc., Cambridge, Mass.) and 3F5 (hybridoma culture supernatant, 0085-P3F5-D5-F8, Dr. Larry Arthur, NCI-Frederick) were previously shown to be reactive with an epitope near the gp120 C5 domain (Moore et al., 1994). The antibody cross-reactive site of human $\alpha_1$PI is contained in the domain Phe-Leu-Met-Ile-Glu-Gln-Asn-Thr-Lys-Ser-Pro-Leu-Phe-Met-Gly-Lys-Val-Val (FLMIEQNTKSPLFMGKVV, aa 372-389, SEQ ID NO: 8) (Bristow et al., 2001) Chimpanzee $\alpha_1$PI, which differs from human $\alpha_1$PI by a single amino acid, Val (aa 385), does not bind anti-gp120, consistent with the ability of chimpanzees to resolve HIV-1 infection and regain normal $CD4^+$ lymphocyte levels. This suggests that the anti-gp120 cross-reactive site in human $\alpha_1$PI is determined primarily by the Met residue (aa 385).

3.3 Expression of recombinant $\alpha_1$PI: Any method known in the art may be used for producing genetically modified $\alpha_1$PI's according to the invention. Two preferred methods are briefly described below for producing such recombinant $\alpha_1$PI's; one method allows expression of $\alpha_1$PI in rice cells and the other allows bacterial expression. The cDNA encoding human α₁PI is obtained from a human cDNA bank by and amplification of the fragment in accession number K01396 using two PCR primers: N-terminal primer 5' GAGGATCCCCAGGGAGATGCTGCCCAGAA 3' (SEQ ID NO: 9) and C-terminal primer 5'CGCGCTCGAGTT-ATTTTTGGGTGGGATTCACCAC 3' (SEQ ID NO: 10) as previously described (Courtney et al., 1984; Terashima et al., 1999; Jean et al., 1998).

For expression in rice cells, expression cassettes are prepared by using a 1.1 kb NheI-PstI fragment, derived from p1AS1.5, is cloned into the vector pGEM5zf- (Promega, Madison, Wis.): ApaI, AatII, SphI, NcoI, SstII, EcoRV, SpeI, NotI, PstI, SalI, NdeI, SacI, MluI, NsiI at the SpeI and PstI sites to form pGEM5zf-(3D/NheI-PstI). The GEM5zf-(3D/NheI-PstI) is digested with PstI and SacI and ligated in two nonkinased 30mers with the complementary sequences 5' GCTTG ACCTG TAACT CGGGC CAGGC GAGCT 3' (SEQ ID NO: 11) and 5' CGCCT AGCCC GAGTT ACAGG TCAAG CAGCT 3' (SEQ ID NO: 12) to form p3DProSig. A 5-kb BamHI-KpnI fragment from lambda clone □OSg1 A is used as a terminator. Hygromycin resistance is obtained from the 3-kb BamHI fragment containing the 35S promoter-Hph-NOS of the plasmid pMON410.

Microprojectile bombardment is applied for transforming a Japonica rice variety TP309. The bombarded calli are then transferred to NB medium containing 50 mg/l hygromycin and incubated in the dark at 25° C. for 10±14 days. Rice cells are cultured at 28° C. (dark) using a shaker with rotation speed 115 rpm in the AA(+sucrose) media. The medium is changed every 5 days to maintain cell lines. AA(−sucrose) is used for α₁PI expression. A bioreactor is used for 2-1-scale culture. The reactor is operated at 28° C. (dark) at agitation speed 30±50 rpm with aeration rate 100 ml/min. During the growth phase (10 days), the pH of the media is controlled at pH 5.7, while in the production phase the PH is 5.7±6.3 (un-controlled).

Recombinant α₁PI is purified using polyclonal anti-human α₁PI antibody (Enzyme Research Laboratories, South Bend, Ind.) immobilized to a CNBr-activated bead-formed agarose-based gel-filtration matrix (Sepharose® 4B) with a concentration of 1.5 mg/ml gel. The gel (3.5 ml) is packed in a column (inner diameter 1.26 cm), and equilibrated with 50 mM Tris-HCl buffer (pH 7.6). Crude medium is applied to the column at 1.0 m./min. Absorbance at 280 nm is monitored at the outlet of the column. After washing with the equilibrium buffer, α₁PI is eluted with 0.1N HCl solution. A peak fraction is collected, and its pH is immediately adjusted with 1M Tris-HCl buffer (pH 8.0). These methods yield an estimated 5.7 mg α₁PI/g dry cell.

Alternatively, the α₁PI cDNA are expressed in *Escherichia coli* strain BL21 transformed with pDS56α₁PI/hf (Invitrogen, Carlsbad, Calif.). Protein expression is induced by addition of 1 mM isopropyl b-D-thiogalactoside, and cultures are grown overnight at 31° C. The cells are washed in metal-chelation chromatography binding buffer (5 mM imidazole/0.5M NaCl/20 mM Tris, pH 7.9) and disrupted by cavitation. The clarified and filtered supernatants containing soluble α₁PI variants are applied to a Ni$^{2+}$-agarose column, and bound proteins are eluted with 100 mM EDTA. The eluates are adjusted to 3.5M NaCl and applied to a hydrophobic interaction chromatography (HIC) column, (phenyl Sepharose®). The bound α1PI/hf is eluted with 20 mM Bis-Tris, pH 7.0 and concentrated (4 mg/ml final) by diafiltration in the same buffer.

4. Genetic modification of active WTI: Recombinant active α1PI is expressed according to the procedures described in Section 3 of the Detailed Description. Wild-type human α₁PI is modified genetically to diminish or enhance sequence-specific reactive sites. For example, in HIV-1 disease, therapeutic α1PI variants maintain its inhibition of soluble HLE$_G$ and its induction of cell migration, but diminish its capacity to facilitate HIV-1 entry and bind antibodies reactive with HIV-1.

The genetic modifications of interest are described in Section 4.1 of the Detailed Description. Site-directed mutagenesis of active α1PI is performed using standard procedures which are well known in the art (e.g., Parfrey et al., 2003; Current Protocols in Molecular Biology, 2002). For example, the DNA sequence encoding the human α1PI signal peptide in pDS56$\alpha_1$PI/hf is replaced with sequences encoding the epitope (FLAG)-tag by insertion of the annealed complimentary oligos 5' CTAGAGGATCCCATGGACTACAAGGACGACGATGACAAGGAA 3' (SEQ ID NO: 13) and 5'GATCTTCCTTGTCATCGTCGTCCTTGTAGTCCATGGGATCCT 3' (SEQ ID NO: 14). The resulting cDNA is subcloned into pDS56-6His to generate pDS56α1PI/hf. To generate pDS56α1PI/hf carrying an amino acid substitution, the DNA sequences encoding the wild-type amino acid are replaced by the complimentary oligos coding for the amino acids described in Section 4.1 of the Detailed Description. The resulting ORFs directed cytosolic expression of the recombinant proteins initiating with a Met followed by the His and FLAG tags and the mature sequences of mutant α1PI.

4.1 Genetic modification within the domain that determines cell migration (FVFLM, aa 370-374, SEQ ID NO: 7) is prepared by site-directed mutagenesis of specific amino acids:

4.1.1 Phe (aa 370) to Ile, Leu, Val, Tyr, or Gly.

4.1.2 Val (aa 371) to Phe, Leu, Ile, or Gly.

4.1.3 Phe (aa 372) to Ile, Leu, Val, Tyr or Gly.

4.1.4 Leu (aa 373) to Ile, Val, Phe, or Gly.

4.1.5 Met (aa 374) to Phe, Thr, Ile, Leu, Val, or Gly.

4.2 Modification within the domain that determines HIV-1 gp120 antibody recognition is prepared by site-directed mutagenesis of Met (aa 385) to Phe, Thr, Be, Leu, Val, or Gly.

5. Proteolytic modification of active or recombinant $\alpha_1$PI: Proteolytic fragments of chemotactic molecules, such as complement, thrombin, and $\alpha_1$PI, impart a primordial system of immune clearance mediators producing discrete classes of cellular responses. The appearance of variant chemotactic molecules avails immediate recruitment of pathogen-responsive immune cells as a direct function of the proteases specific to each pathogen. To replicate this system for therapeutic application, active or recombinant $\alpha_1$PI are modified proteolytically to diminish or enhance conformation-specific reactive sites.

Cleavage of $\alpha_1$PI producing inactive $\alpha_1$PI maybe accomplished using a variety of proteinases. Cleavage by elastase is between Met-Ser (aa 358-359) (Berninger, 1985), and by stromelysin-3, a stromal cell-derived matrix metalloproteinase (MMP), between Ala-Met (aa 350-351) (Pei et al., 1994). Cleavage of $\alpha_1$PI by neutrophil collagenase or gelatinase is between Phe-Leu (aa 352-353) producing inactive $\alpha_1$PI (Desrochers et al., 1992). Other MMPs have also been shown to cleave $\alpha_1$PI (Mast et al., 1991). Significantly, $\alpha_1$PI is cleaved by proteinase derived from pathogenic organisms such as *Pseudomonas elastase* (Barbey-Morel and Perlmutter, 1991).

The C-terminal $\alpha_1$PI proteolytic fragments acquire attributes that allow interaction with the LDL receptor-related protein (LRP) (Poller et al., 1995) and other receptors that recognize a pentapeptide sequence FVFLM (aa 370-374, SEQ ID NO: 7) (Joslin et al., 1992) in a manner that produces, chemotaxis of neutrophils, increased LDL binding to monocytes, upregulated LDL receptors, increased cytokine production, and $\alpha_1$PI synthesis (Banda et al., 1988; Janciauskiene et al., 1999; Janciauskiene et al., 1999). It has been shown that fibrillar aggregates of the C-terminal fragment of $\alpha_1$PI facilitate uptake of LDL by LRP on the hepatolastoma cell line HepG2 (Janciauskiene and Lindgren, 1999), and these fragments participate in atherosclerosis (Dichtl et al., 2000).

Specifically, active or recombinant $\alpha_1$PI are incubated at the relevant optimal conditions with one or a combination of pepsin, plasmin, urokinase, chymotrypsin, thrombin, CD26, matrix metalloproteinases, complement components C1 or C3, and other proteinases that facilitate the generation of chemotactic fragments of $\alpha_1$PI (Methods in Enzymology, 1970; Hooper, 2002). Cleavage of $\alpha_1$PI is then terminated by changing the optimal conditions in the proteinase mixture to conditions that prevent proteinase activity, for example at temperature or pH extremes (Methods in Enzymology, 1970; Hooper, 2002).

6. Functional capacity of active, genetically modified, and proteolytically modified $\alpha$1PI: Various unmodified and modified $\alpha_1$PI's are screened and selected for use in treatment of specific diseases by determining their capacity in vitro and/or in vivo to perform the following functions in the following assays:

6.1 Inhibit elastase: The procedures for measuring the capacity of $\alpha_1$PI to inhibit soluble forms of porcine pancreatic elastase (PPE) or $HLE_G$ are well established (U.S. Pat. No. 6,887,678) (Bristow et al., 1998). Briefly, PPE is incubated for 2 min with $\alpha$1PI, and to this mixture is added, the elastase substrate succinyl-L-Ala-L-Ala-L-Ala-p-nitroanilide ($SA^3NA$). Results are detected by measuring the color change at 405 nm.

In complex mixtures, $\alpha_1$PI competes for binding to PPE with other proteinase inhibitors or ligands present in the mixture. For example, PPE has higher affinity for $\alpha_2$macroglobulin ($\alpha_2$M) than for $\alpha_1$PI, and when complexed with $\alpha_2$M, PPE retains the ability to cleave small substrates. In the presence of $\alpha_2$M, PPE binds $\alpha_2$M and is protected from inhibition by $\alpha_1$PI, and the complexation of PPE with $\alpha_2$M can be measured by detecting the activity of PPE using $SA^3NA$. To measure the inhibitory capacity of $\alpha_1$PI in complex mixtures such as serum, two-fold serial dilutions of serum are incubated with a constant, saturating concentration of PPE. The added PPE is bound by, $\alpha_2$M and $\alpha_1$PI in the diluted serum dependant on their concentrations, the greater the concentration of serum, the greater the concentration of $\alpha_2$M and $\alpha_1$PI. Since there is more $\alpha_1$PI in serum than $\alpha_2$M, as serum is diluted, $\alpha_2$M is diluted out, and in the absence of $\alpha_2$M, PPE is bound and inhibited by $\alpha_1$PI. The complexation of PPE with $\alpha_1$PI can be measured by detecting the loss of activity of PPE using $SA^3NA$. As serum is further diluted, $\alpha_1$PI is also diluted out, and the loss of complexation of PPE with $\alpha_1$PI can be measured by detecting the gain in activity of PPE using $SA^3NA$. The plot of PPE activity versus serum dilution makes a V shaped curve, PPE activity first decreasing as serum is diluted, and then increasing as serum is further diluted. The nadir of PPE activity is used to calculate the precise concentration of active $\alpha_1$PI in the mixture (Bristow et al., 1998).

6.2 Induce receptor co-capping and cell motility: The procedures for inducing receptor capping have been described (Bristow et al., 2003). The cells of interest (monocytes, lymphocytes, neutrophils, or other blood cells, e.g. leukemic cells) are isolated from blood or tissue using standard techniques (Messmer et al., 2002) and examined for reactivity with $\alpha_1$PI.

To examine receptor capping, cells are incubated with active or modified $\alpha_1$PI for 15 min in humidified 5% $CO_2$ at 37° C. Cells are applied to the sample chambers of a cytospin apparatus (Shandon Inc. Pittsburgh, Pa.), and slides are centrifuged at 850 rpm for 3 min. Slides are fixed by application of 50 μl 10% formalin to the sample chambers of the cytospin apparatus followed by an additional centrifugation at 850 rpm for 5 min. Slides are incubated for 90 min at 20° C. with fluorescently-labeled monoclonal antibodies having specificity for the receptors of interest and examined by microscopy.

Cell motility results from selective and sequential adherence and release produced by activation and deactivation of receptors (Wright and Meyer, 1986; Ali et al., 1996), consequent polar segregation of related membrane proteins to the leading edge or trailing uropod, and both clockwise and counterclockwise propagation of $Ca^{++}$ waves which initiate from different locations in the cell (Kindzelskii and Petty, 2003). Thus, several aspects of the complex process may be quantitated. The most direct and most easily interpreted method for quantitating cell motility is the enumeration of adherent cells in response to a chemotactic agent such as $\alpha_1$PI.

For detecting adherence, sterile coverslips are washed in endotoxin-free water, and to each coverslip is delivered various dilutions of active or modified $\alpha_1$PI. Cells are subsequently delivered to the coverslips, mixed to uniformity with $\alpha_1$PI, and incubated for 30 min in humidified 5% $CO_2$ at 37° C. without dehydration. After stringently washing the coverslips free of non-adherent cells, adherent cells are fixed by incubation for 10 min at 20° C. with 4% paraformaldehyde containing 2.5 mM of the nuclear staining fluorescent dye, acridine orange (3,6-bis[dimethylamino] acridine. Slides are examined by microscopy, and means and standard deviations are determined by counting adherent cells in at least three fields/coverslip.

6.3 Mobilize lymphoid-committed progenitor cells: In the nonobese diabetic/severe combined immunodeficiency (NOD/SCID) mouse model, bone marrow-engrafted human cells can be mobilized by G-CSF (Petit et al., 2002). This model is adapted to assess the capacity of active or modified $\alpha_1$PI to mobilize human lymphoid- or myeloid-lineage cells, respectively.

NOD/SCID mice are housed under defined flora conditions in individually ventilated (HEPA-filtered air) sterile micro-isolator cages. Human chimeric mice are obtained after sublethal irradiation (375 cGy at 67 cGy/min) and injection of $2\times10^7$ human cord blood mononuclear cells. Four to five weeks post transplantation, mobilization is performed by application of either G-CSF or $\alpha_1$PI. For mobilization of myeloid-committed progenitors, mice receive daily subcutaneous injections of 300 mg/kg G-CSF (Filgrastim, Neupogen® or Neulasta®, Amgen, Inc.) in 250 μl of 0.9% NaCl, 5% fetal calf serum for 4-5 days. Alternatively, mice receive twice weekly infusion via the dorsal tail vein of inactive or modified $\alpha_1$PI (39 mg/kg) at a rate of 0.08 ml/kg/minute. For mobilization of lymphoid-committed progenitors, mice receive twice weekly infusion via the dorsal tail vein of active or modified $\alpha_1$PI (42 mg/kg) at a rate of 0.08 ml/kg/minute. Mice are asphyxiated with dry ice, peripheral blood is collected by cardiac aspiration into heparinized tubes, and bone marrow is harvested, and cells are flushed from femurs and tibias into single-cell suspensions. Peripheral blood and bone marrow cells are analyzed by flow cytometry for the presence of myeloid and lymphoid markers including CD34 CD38, CD10, CD11b, CD11c, CD13, CD14, CD19, CD3, CD4, CD8, CD45, CD184 (CXCR4), CD66, and $HLE_{CS}$ (U.S. Pat. No. 6,858,400).

6.4 Bind anti-HIV-1 gp120: Active or modified $\alpha_1PI$ are incubated in fluid phase with monoclonal antibodies reactive with HIV-1 gp120. The anti-gp120 monoclonal antibodies 3F5 (hybridoma culture supernatant, 0085-P3F5-D5-F8) is reactive with an epitope near the gp120 C5 domain (Moore et al., 1994). Clone α70 (ICN Biochemicals, Aurora, Ohio) is reactive with the V3-loop of gp120, a domain that is identical to the HLE ligand inter-α-trypsin inhibitor (Pratt et al., 1987). Immune complexes are captured by incubating mixtures in wells of a microtiter plate pre-coated with chicken anti-human $\alpha_1PI$ IgG. Binding is detected using horse radish peroxidase-conjugated rabbit anti-mouse IgG followed by substrate, orthophenylene diamine HCl.

6.5 Facilitate HIV-1 infectivity: Primary non-syncytium inducing HIV-1 clinical isolates (Advanced Biotechnologies, Rivers Park, Ill.) are used to infect peripheral blood mononuclear cells maintained in wells of a 96 well tissue culture plate at $2 \times 10^6$ cells/ml in RPMI-1640 containing 20% autologous serum and 10% IL-2 (Cellular Products, Buffalo, N.Y.). Prior to addition of HIV-1, cells are incubated with active or modified $\alpha_1PI$ for 0 min or 60 min at 37° C., 5% $CO_2$. In vitro infectivity outcome is determined in triplicate by p24 accumulation or by RT activity as previously described (Bristow, 2001). Cell counts and viability are determined at the final time point.

7. Treatment outcome measurements:

7.1 To determine the effectiveness of treatment on elastase inhibitory capacity, individuals are monitored weekly for active and inactive $\alpha_1PI$ blood levels (Bristow et al., 1998) (U.S. Pat. No. 6,887,678). Briefly, a constant amount of active site-titrated PPE is allowed to incubate with serial dilutions of serum for 2 min at 37° C. after which a PPE substrate is added. Determination of the molecules of substrate cleaved by residual, uninhibited PPE is used to calculate the molecules of active and inactive $\alpha_1PI$ in blood.

7.2 To determine the effectiveness of treatment on inducing changes in levels of targeted blood cell populations, treated individuals are monitored weekly for changes in complete blood count and differential, as well as for changes in specific subsets of blood cells such as $CD4^+$ cells and $HLE_{CS}^+$ cells using flow cytometry (Bristow et al., 2001; Bristow, 2001) (U.S. Pat. No. 6,858,400). Briefly, 100 μl of whole blood is incubated with a panel of fluorescently-labeled monoclonal antibodies approved by the FDA for medical diagnostics. These antibodies are selected to specifically recognize the cell receptors that uniquely identify the cell population of interest. Identification and enumeration of the cells in blood that are bound to the monoclonal antibodies is performed using flow cytometry.

7.3 To determine the influence of treatment on disease progression, individuals are monitored for the specific pathologic determinants of disease which are well known in the art for the various indications, e.g. in stem cell transplantation, organ transplantation, autoimmunity, diabetes, leukemia, cancer, HIV-1 infection, atherosclerosis, and other diseases influenced by blood cells. For example, in HIV-1 disease, individuals are monitored for changes in $CD4^+$ lymphocyte levels and HIV levels (Bristow et al., 2001; Bristow, 2001), In leukemia or cancer, individuals are monitored for changes in the presence of leukemic or cancerous cells (Tavor. S. et al., 2005). In stem cell transplantation, individuals are monitored for changes in normal blood cells (Jansen et al., 2005). In organ transplantation, individuals are monitored for organ rejection (Kirschfink, 2002). In autoimmunity, individuals are monitored for the presence of autoantibodies and specific functions of the affected organs (Marinaki et al., 2005). In diabetes and atherosclerosis, individuals are monitored for changes in total cholesterol, LDL, HDL, and triglyceride levels (Talmud et al., 2003).

EXAMPLES

1. Increased $CD4^+$ lymphocytes are correlated with increased $\alpha_1PI$ and decreased $HLE_{CS}^+$ lymphocytes in healthy individuals. In healthy individuals, circulating $\alpha_1PI$ ranges from 18-53 μM between the $5^{th}$ and $95^{th}$ percentiles, and 90-100% of this protein is in its active form as determined by inhibition of porcine pancreatic elastase (Bristow et al., 2001). To investigate the relationship between active $\alpha_1PI$, $HLE_{CS}^+$, and $CD4^+$ lymphocytes, 6 healthy HIV-1 seronegative adults, 3 males and 3 females, were specifically selected to represent a wide spectrum of $\alpha_1PI$ (1.9-61.5 μM). Subjects were measured for CD4, CXCR4, CCR5, $HLE_{CS}$, active and inactive $\alpha_1PI$ levels, and $\alpha_2$-macroglobulin ($\alpha_2M$). Independently, neither active $\alpha_1PI$, $HLE_{CS}^+$ lymphocytes, $\alpha_2M$, $CXCR4^+$ lymphocytes, nor $CCR5^+$ lymphocytes were correlated with $CD4^+$ lymphocytes. However, by multilinear regression analysis, it was found that higher numbers of $CD4^+$ lymphocytes (% lymphocytes) were correlated ($r^2=0.937$) with two counterbalancing variables together, higher active $\alpha_1PI$ (p=0.008) and lower $HLE_{CS}^+$ lymphocytes (p=0.034) (FIG. 1a).

To investigate $CD4^+$ lymphocyte levels in the general population, blood was collected from an additional 18 healthy, HIV-1 seronegative adults, 9 males and 9 females, who were measured for CD4, CXCR4, CCR5, SDF-1, active and inactive $\alpha_1PI$ levels. $HLE_{CS}$ was measured in 16 of these individuals. Values for active $\alpha_1PI$ (19-37 μM) and SDF-1 levels (191-359 pM) for these volunteers were found to be within normal ranges. Higher $CD4^+$ lymphocytes (%) were again found to be correlated ($r^2=0.803$) with higher active $\alpha_1PI$ (p<0.007) and lower $HLE_{CS}^+$ lymphocytes (p<0.001) (FIG. 1b). Along with active $\alpha_1PI$ and $HLE_{CS}^+$ lymphocytes, lower SDF-1 concentration (p=0.02) also significantly contributed to predicting higher $CD4^+$ lymphocytes ($r^2=0.875$). Although $CXCR4^+$ lymphocytes were not significantly related to $CD4^+$ lymphocytes, this may reflect the detection of both active and inactive configurations of CXCR4 on individual cells (Percherancier et al., 2005).

There was no statistical difference between the volunteers in FIGS. 1a and b in their active $\alpha_1PI$ levels (median=23 and 24, respectively) and $CD4^+$ lymphocytes (mean=48% and 45%, respectively); however, in volunteers depicted in FIG. 1a the range is wide (1.9-61.5 μM) and standard deviation is large (s=24), whereas in volunteers depicted in FIG. 1b, the range of active $\alpha_1PI$ is narrow (19-37 μM) and the standard deviation is small (s=6), and this suggests $CD4^+$ lymphocyte levels are sensitive to small differences in $\alpha_1PI$ levels. The sensitivity of $CD4^+$ lymphocyte levels to $\alpha_1PI$ levels is further exemplified during the acute phase of an enteric infection in one volunteer who was otherwise healthy (FIG. 1c). In this individual, an increase in total lymphocytes (1.15-fold) and $CD4^+$ lymphocytes (1.2 fold) was found to occur in concert with an increase in total $\alpha_1PI$ (2.7-fold), increase in active $\alpha_1PI$ (1.5 fold), and decrease in $HLE_{CS}$ (2.9-fold).

Figure 4:
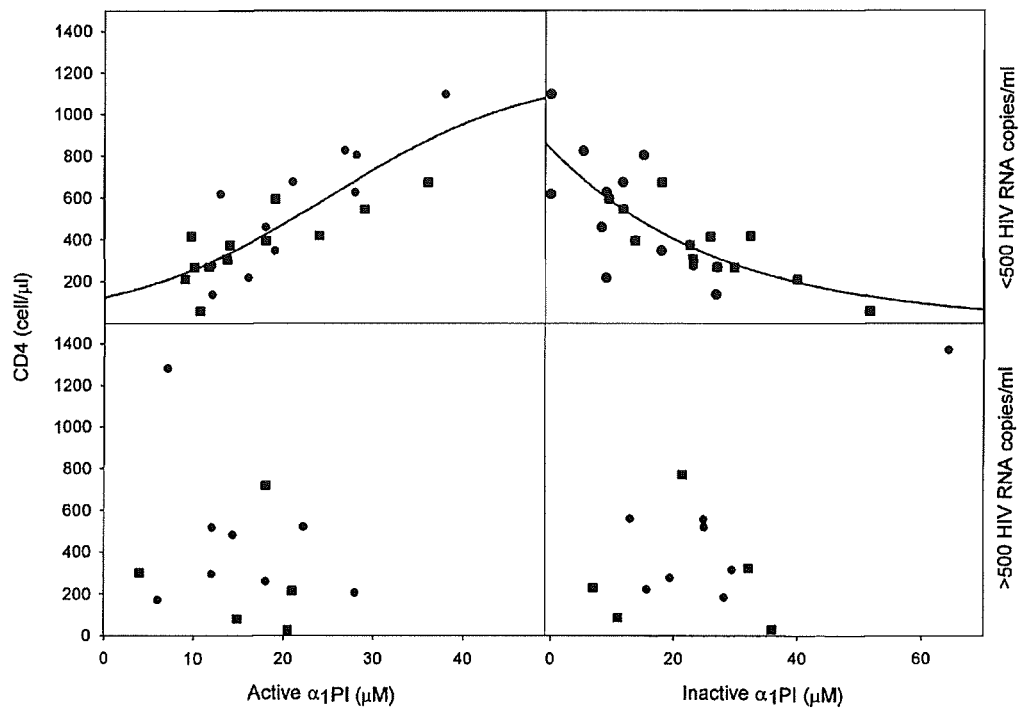
FIG. 4. Correlation between CD4$^+$ lymphocytes and active $\alpha_1$PI levels in HIV-1 infected patients. In 23 patients with <500 HIV RNA copies/ml, CD4$^+$ lymphocyte levels correlate with active $\alpha_1$PI. Three parameter sigmoid regression yields CD4 (cells/μl)=1+$e^{-(active\ \alpha1PI(\mu M)-25)/11}$), $r^2$=0.927, n=23). CD4$^+$ lymphocyte levels also correlate with inactive $\alpha_1$PI. Two parameter exponential decay regression yields CD4 (cells/μl)=834*$e^{-0.034\ inactive\ \alpha1PI(\mu M)}$, $r^2$=0.906, n=23). Patients receiving protease inhibitor therapy are depicted by squares. All other patients are depicted by circles. In 13 patients with >500 HIV RNA copies/ml, no correlation was found to exist between CD4$^+$ lymphocyte levels and active $\alpha_1$PI.

2. Monoclonal anti-gp120 binds human, but not chimpanzee $\alpha_1PI$. Two monoclonal antibodies (1C1 and 3F5) which bind a conformationally determined epitope near the C5 domain of gp120 (Moore et al., 1994) were found to also bind human $\alpha_1$PI (Bristow et al., 2001). It was hypothesized that anti-gp120 mediated depletion of active $\alpha_1$PI might be pathognomonic for HI-1 AIDS. If true, chimpanzee $\alpha_1$PI should differ from human $\alpha_1$PI since HIV-1 infected chimpanzees survive infection and regain normal levels of $CD4^+$ lymphocytes (Rutjens et al., 2003). Sequence comparison revealed that human $\alpha_1$PI differs from chimpanzee $\alpha_1$PI by one amino acid (aa 385) caused by a single nucleotide change (NCBI accession numbers BT019455 and XP_522938), and this aa difference lies in the gp120-homologous region of $\alpha_1$PI. To determine whether this sequence difference affects the binding of anti-gp120 to $\alpha_1$PI, 20 human and 20 chimpanzee sera were compared. Both 1C1 (data not shown) and 3F5 exhibited 8- to 14-fold greater binding to human, than chimpanzee $\alpha_1$PI in 6 repeat measurements (p<0.001) (FIG. 2*a*). Negative control monoclonal antibody $\alpha$70 which reacts with the V3-loop of gp120 failed to bind human $\alpha_1$PI (data not shown) consistent with previous findings (Bristow et al., 2001). Serum $\alpha_1$PI in two human subjects exhibited much greater affinity for 3F5 than that from other subjects, and this suggests the epitope of $\alpha_1$PI recognized by 3F5 may be phenotypically determined. When these two subjects were omitted from the comparison, the statistical difference between binding of 3F5 to human or chimpanzee $\alpha_1$PI was maintained (p<0.001).

To examine the relationship between lower $CD4^+$ lymphocyte levels and lower active $\alpha_1$PI levels in HIV-1 disease, blood from 38 HIV-1 infected patients was analyzed. Of these 38 patients, 29% had detectable IgG-$\alpha_1$PI immune complexes, 89% were on antiretroviral therapy, and 60% had <500 HIV-1 RNA copies/ml (FIG. 2*b*). The number of patients exhibiting detectable IgG-$\alpha_1$PI immune complexes in this study differs from a previous study of 68 HIV-1 patients in which 60% had detectable IgG-$\alpha_1$PI immune complexes, 53% were on antiretroviral therapy (AZT only), and 16% had <500 HIV-1 RNA copies/ml (Bristow et al., 2001). This reason for this difference may be related to the improved antiretroviral therapy in place today.

None of the sera from healthy chimpanzees, nor sera collected from 2 chimpanzees post-HIV-1 inoculation, had evidence of detectable IgG-$\alpha_1$PI immune complexes. The HIV-1 inoculated chimpanzees were confirmed to be HIV-1 infected, but had normal $CD4^+$ lymphocytes (Girard et al., 1998). In addition, despite the presence of anti-gp120, we found no evidence of IgG-$\alpha_1$PI immune complexes in 10 rhesus macaques following immunization with simian/human immunodeficiency virus (SHIV 89.6) gp120 or gp140, or in 3 macaques infected with SHIV (data not shown). Extensive in vitro analyses failed to demonstrate bi-molecular complexes between gp120 and $\alpha_1$PI (data not shown), and the absence of detection of IgG-$\alpha_1$PI immune complexes in sera from HIV-1 infected chimpanzees suggests gp120 and $\alpha_1$PI are not associated by aggregation in sera. These results suggest that IgG-$\alpha_1$PI immune complexes are unique to HIV-1 disease in humans.

Consistent with evidence from a previous patient study, active $\alpha_1$PI in the HIV-1 infected patients was significantly below normal (median 17 μM, p<0.001) (FIG. 2*c*) and inactive $\alpha_1$PI was significantly above normal (median 19 μM, p<0.001) (FIG. 2*d*) (Bristow et al., 2001). In contrast to humans, active $\alpha_1$PI levels in sera collected from the 2 chimpanzees post-HIV-1 inoculation (39 μM) were not different from normal chimpanzee and human sera (p=0.810) (FIG. 2*c*).

To determine whether $\alpha_1$PI becomes inactivated after complexing with the 3F5 anti-gp120 monoclonal antibody, 3F5 was incubated with sera samples from five healthy individuals. In comparison to untreated sera, $\alpha_1$PI activity was significantly diminished to the same degree in all sera (mean difference=5.8±0.5 μM, p<0.001) (FIG. 2*e*).

The gp120 epitope recognized by 1C1 and 3F5 is considered to be conformation-dependent (Moore et al., 1994). The gp120 peptide immunogen used to raise 1C1 and 3F5 (aa 300-321, GGGDMRDNWRSELYKYKVVK (SEQ ID NO: 15) (Ratner et al., 1985) contains both an $\alpha$-helix (aa 306-313) and linear strand (aa 314-321) (FIG. 3*a,b*), but other epitope determinants of the antibodies are not known. In human $\alpha_1$PI (FIG. 3*c,d*), the gp120-homologous sequence (aa 369-389, PFVFLMIDQNTKSPLFMGKVV (SEQ ID NO: 16) folds to form a two-stranded antiparallel $\beta$-sheet that lies at the base of a cleft (4A° deep by 20A° long by 5A° wide) topped by two $\alpha$-helices (aa 28-47 and 259-277) in a smaller, but similar configuration as the antigen-binding cleft of MHC (10A° deep by 25A° long by 10A° wide) (Bjorkman et al., 1987). At the far end of the first of these $\alpha$-helices is the N-linked mannose-containing oligosaccharide that confers structural polymorphism to $\alpha_1$PI (aa 46) (Jeppsson et al., 1985). In the center of the $\alpha$-sheet that lies in the cleft, is M-385 which distinguishes human from chimpanzee $\alpha_1$PI (V-385): The function of this cleft is not known, but a sequence in the center of the $\beta$-sheet formation (aa 370-374, FVFLM (SEQ ID NO: 7) is homologous to the fusion domain of HIV-1 gp41, and this sequence has been implicated in binding $HLE_{CS}$ (Bristow et al., 1995; Bristow et al., 2003) and stimulating cell motility (Joslin et al., 1991).

In $\alpha_1$PI, the sequence GKVV (aa 386-389, SEQ ID NO: 2) lies within 5A° of M-385, N-46, and the N-linked oligosaccharide in a space occupying 5A° by 5A° by 5A°. In gp120, in the same relative orientation as in $\alpha_1$PI, the sequence YKVV (aa 315-318, SEQ ID NO: 1) lies within 5A° of M-17 and 8A° of N-92 and the N-linked mannose-containing oligosaccharide (Leonard et al., 1987) in a space occupying 5A° by 5A° by 8A°. Evidence that $\alpha_1$PI polymorphisms may influence 3F5 binding (FIG. 2*a*) suggests the polymorphism-determining N-46 oligosaccharide participates in 3F5 recognition of $\alpha_1$PI. Thus, the 3F5 conformational epitope is suggested by these analyses to occupy a 5A° by 5A° by 8A° space including KVV, M, N, and the N-linked oligosaccharide. This proposed conformational epitope is consistent with previously characterized antigen configurations that contain oligosaccharide determinants (Cygler et al., 1991) as well as with results demonstrating that gp120 N-92 is invariant (Wei et al., 2003).

3. Active $\alpha_1$PI is rate limiting for $CD4^+$ lymphocytes in HIV-1 disease. Of the 36 patients included in the study population, 23 were below 500 and 13 were above 500 HIV RNA copies/ml at the time of blood collection. All patients were measured for CD4, CXCR4, CCR5, SDF-1 levels, active and inactive $\alpha_1$PI. Only 28 of these patients were additionally measured for $HLE_{CS}$. Neither CXCR4 nor CCR5 were found to correlate individually or in combination with any parameters of disease being investigated in these patients. Eleven of the 38 HIV-1 patients had active liver disease as defined by detectable Hepatitis B or C, or elevated liver enzymes. HIV-1 patients with liver disease were not different from patients without liver disease in active $\alpha_1$PI (p=0.95), total $\alpha_1$PI (p=0.79), CXCR4 (p=0.63), or CCR5 (p=0.9), but exhibited significantly higher SDF-1 (p<0.001), $HLE_{CS}^+$ lymphocytes (p<0.001), and $CD4^+$ lymphocytes (p=0.04).

In the 23 patients with <500 HIV-1 RNA copies/ml, higher $CD4^+$ lymphocyte levels were correlated with higher active $\alpha_1$PI concentration ($r^2$=0.927) and lower inactive $\alpha_1$PI concentration ($r^2$=0.946) (FIG. 4). Prediction of CD4 levels from active $\alpha_1$PI levels with 95% confidence had a standard error of 151 cells/μl, and prediction from inactive $\alpha_1$PI levels with 95% confidence had a standard error of 105 cells/4 Of these 23 patients, only 16 had been additionally measured for HLE$_{CS}$. As in Healthy individuals (FIG. 1), lower HLE$_{CS}^+$ lymphocytes was itself not correlated with higher CD4$^+$ lymphocytes, but in combination with higher active $\alpha_1$PI was significantly correlated (p=0.01). That CD4$^+$ lymphocyte levels could be predicted by active $\alpha_1$PI alone with such a high degree of accuracy in patients controlling their viral load suggests that, unlike the normal population, active $\alpha_1$PI is rate limiting for CD4$^+$ lymphocyte levels in HIV-1 disease. In patients with >500 HIV RNA copies/ml, there was no relationship between CD4$^+$ lymphocyte levels and active or inactive $\alpha_1$PI (FIG. 4), and this suggests either HIV-1 itself, or other host processes had contributed to disrupting the regulation of CD4$^+$ lymphocyte levels.

4. $\alpha_1$PI augmentation therapy in HIV-1 infected patients. The number of CD4$^+$ T lymphocytes in patients with <500 HIV-1 RNA copies/ml is controlled by their circulating concentration of $\alpha_1$PI (Example 2). These patients have below normal levels of circulating $\alpha_1$PI (Bristow et al., 2001). Approximately 10% clinic patients in New York City who have <500 HIV-1 RNA copies/ml also have <200 CD4 cells/μl, and these patients benefit from $\alpha_1$PI augmentation by increasing their CD4$^+$ T lymphocyte numbers. Treatment of HIV-1 infected patients with $\alpha_1$PI augmentation is indicated in patients who are simultaneously receiving one or a combination of the four currently known classes, nucleoside reverse transcriptase inhibitors, non-nucleoside reverse transcriptase inhibitors, HIV-1 aspartyl protease inhibitors, and fusion inhibitors.

Patients with <500 HIV-1 RNA copies/ml and <200 CD4 cells/μl who are receiving antiretroviral therapy are treated using Zemaira® $\alpha_1$PI. Patients receive weekly infusions of Zemaira® at 60 mg/kg as described in Section 2 of the Detailed Description. Treatment outcome is monitored as described in Section 7.3 of the Detailed Description. Specifically, patients receiving Zemaira® are monitored weekly for changes in active and inactive $\alpha_1$PI levels as well as for CD4$^+$ T lymphocytes and other subsets of circulating blood cells. Patients are also monitored for changes in HIV-1 RNA copies/ml, LDL, HDL, cholesterol, triglycerides, and the occurrence of infections designated by the CDC as parameters of HIV-1 disease progression (Castro et al., 1992). To determine possible adverse effects of immune complex disease, individuals are monitored for the presence of antibodies reactive with $\alpha_1$PI as well as for the occurrence of glomerulonephritis by measuring either proteinuria or serum creatinine levels (Bristow et al., 2001; Virella et al., 1981).

5. $\alpha_1$PI augmentation therapy in HIV-1 infected patients using genetically modified $\alpha_1$PI. Antibodies that recognize HIV-1 are the only diagnostic marker of infectivity. The presence of an anti-gp120 antibody that also binds $\alpha_1$PI has been detected in most HIV-1 infected individuals (Bristow et al., 2001), and this antibody inactivates and produces deficient levels of $\alpha_1$PI. Anti-gp120 does not bind chimpanzee $\alpha_1$PI which differs from human $\alpha_1$PI by a single amino acid (aa 385) (Example 2). To therapeutically augment $\alpha_1$PI in HIV-1 infected individuals, it is desirable to use genetically modified $\alpha_1$PI which substitutes a different aa in place of Met (aa 385). In addition, a hydrophobic domain (aa 370-374) near Met (aa 385) has been shown to facilitate HIV-1 entry (Bristow et al., 2001). Thus, it is also desirable to change one or more of the aa in this hydrophobic domain for treatment in HIV-1 disease.

$\alpha_1$PI is genetically modified as described in Section 4 of the Detailed Description with three substitutions, aa 385 (Met to Val), aa 372 (Phe to Gly), and aa 373 (Leu to Gly), and is designated $\alpha_1$PI.β.F372G.L373G.M385V ($\alpha_1$PI.β. The $\alpha_1$PI.β sequence with aa changes represented in bold underlined letters is as follows (SEQ ID NO: 17):

```
 -24  MPSSVSWGIL LLAGLCCLVP VSLA

1  EDPQGDAAQK TDTSHHDQDH PTFNKITPNL AEFAFSLYRQ LAHQSNSTNI

51  FFSPVSIATA FAMLSLGTKA DTHDEILEGL NFNLTEIPEA QIHEGFQELL

101  RTLNQPDSQL QLTTGNGLFL SEGLKLVDKF LEDVKKLYHS EAFTVNFGDT

151  EEAKKQINDY VEKGTQGKIV DLVKELDRDT VFALVNYIFF KGKWERPFEV

201  KDTEEEDFHV DQVTTVKVPM MKRLGMFNIQ HCKKLSSWVL LMKYLGNATA

251  IFFLPDEGKL QHLENELTHD IITKFLENED RRSASLHLPK LSITGTYDLK

301  SVLGQLGITK VFSNGADLSG VTEEAPLKLS KAVHKAVLTI DEKGTEAAGA

351  MFLEAIPMSI PPEVKFNKPF VGGMIEQNTK SPLFVGKVVN PTQK
```

The functional capacity of $\alpha_1$PI.β depicted in Table 2 is determined as described in Section 6 of the Detailed Description.

TABLE 2

Functions of the C-terminal region of $\alpha_1$PI.β

| | Proteinase Inhibition | Lymphoid cell migration | Myeloid cell migration | anti-gp120 binding | HIV-1 entry co-factor |
|---|---|---|---|---|---|
| Native configuration in the active $\alpha_1$PI.β | + | − | − | − | + |
| Rearranged configuration in cleaved $\alpha_1$PI.β | − | − | − | − | − |

TABLE 2-continued

Functions of the C-terminal region of $\alpha_1$PI.$\beta$

| | Proteinase Inhibition | Lymphoid cell migration | Myeloid cell migration | anti-gp120 binding | HIV-1 entry co-factor |
|---|---|---|---|---|---|
| Complexed with HLE in cleaved $\alpha_1$PI.$\beta$ | − | − | − | − | − |
| Independent of other $\alpha_1$PI.$\beta$ cleavage products | − | − | − | − | Unknown |

The recommended dose of $\alpha_1$PI is 60 mg/kg. The specific activity of Zemaira® is 70%, where specific activity is defined as inhibition of PPE (Bristow et al., 1998). Thus, the recommended dose of Zemaira® $\alpha_1$PI may be stated as 42 mg/kg active $\alpha_1$PI. In accordance with the recommended Zemaira® treatment regimen, HIV-1 patients with <500 HIV-1 RNA copies/ml and <200 CD4 cells/µl who are receiving antiretroviral therapy are infused with the concentration of $\alpha_1$PI.$\beta$ that is in the range of 1 to 420 mg/kg active $\alpha_1$PI with a target blood threshold of 35 µM $\alpha_1$PI.$\beta$. Treatment of HIV-1 infected patients with $\alpha_1$PI.$\beta$ is indicated in patients who are simultaneously receiving one or a combination of the four currently known classes, nucleoside reverse transcriptase inhibitors, non-nucleoside reverse transcriptase inhibitors, HIV-1 aspartyl protease inhibitors, and fusion inhibitors. Treatment outcome is monitored as described in Section 7.3 of the Detailed Description. Specifically, patients receiving $\alpha_1$PI.$\beta$ are monitored weekly for changes in active and inactive $\alpha_1$PI levels as well as for $CD4^+$ T lymphocytes and other subsets of circulating blood cells. Patients are also monitored for changes in HIV-1 RNA copies/nil, LDL, HDL, cholesterol, triglycerides, and the occurrence of infections designated by the CDC as parameters of HIV-1 disease progression (Castro et al., 1992). To determine possible adverse effects of immune complex disease, individuals are monitored for the presence of antibodies reactive with $\alpha_1$PI as well as for the occurrence of glomerulonephritis by measuring either proteinuria or serum creatinine levels (Bristow et al., 2001; Virella et al., 1981).

6. $\alpha_1$PI inhibits SDF-1 induced migration of human leukemic cells in, but enhances migration of human stem cells. Human acute myeloid leukemia cells (AML) not only secrete $HLE_G$, but also express $HLE_{CS}$ constitutively on the cell surface in a manner that is regulated by the CXCR4/SDF-1 axis (Tavor. S. et al., 2005). Preincubation of AML cells with $\alpha_1$PI significantly reduced their SDF-1 dependent migration in all AML cells tested using an in vitro transwell assay (Tavor. S. et al., 2005). Further, in a mouse model it was found that $\alpha_1$PI inhibited homing of transplanted human stem cells to bone marrow and egress of transplanted AML cells from bone marrow. The influence of $\alpha_1$PI was shown to occur by its action on $HLE_{CS}$. When AML cells were treated with $\alpha_1$PI, SDF-1 induced pseudopodia formation was prevented. These results are in contrast to previous studies using a U937 promonocytic cell line which demonstrated that $\alpha_1$PI-induced pseudopodia formation was prevented by pretreatment with SDF-1 (Bristow et al., 2003), and this difference emphasizes the importance of $\alpha_1$PI and SDF-1 in promoting cell migration of various cells dependent on their stage of differentiation. Augmentation with active and modified $\alpha_1$PI is used therapeutically to control the proliferation and spread of leukemia and lymphoma cells. Active $\alpha_1$PI is used to prevent proliferation and spread of leukemia and lymphoma cells triggered by SDF-1. Inactive $\alpha_1$PI is used to prevent proliferation and spread of leukemia and lymphoma cells triggered by active $\alpha_1$PI. Patients receive therapeutic augmentation with active or modified $\alpha_1$PI with a target blood threshold of 35 µM active $\alpha_1$PI and are monitored for active and inactive $\alpha_1$PI levels as well as for changes in the number of AML cells in circulation using flow cytometry.

7. $\alpha_1$PI augmentation therapy in patients with a microbial infection. High levels of neutrophils and $HLE_G$ are present in the respiratory secretions of patients with cystic fibrosis. The primary cause of this inflammatory situation is chronic infection with *Pseudomonas aeruginosa* and other bacteria. Abundant $\alpha_1$PI is present in these patients, but is predominantly inactivated by $HLE_G$ and *P. aeruginosa* elastase (Barbey-Morel and Perlmutter, 1991). Prolastin® has demonstrated improvement by reducing elastase activity, neutrophil counts, and bacterial colonies in a rat model (Cantin and Woods, 1999). Inactivated $\alpha_1$PI is a chemoattractant for neutrophils (Joslin et al., 1992). In addition to the therapeutic benefit of inhibiting the elevated elastase activity that attends the inflammatory sequelae of microbial infection, augmentation with active $\alpha_1$PI diminishes the inactivated $\alpha_1$PI-induced neutrophil infiltrate. Patients receive active $\alpha_1$PI with a target blood threshold of 35 µM active $\alpha_1$PI and are monitored for active and inactive $\alpha_1$PI levels as well as for changes in the number of neutrophils in circulation using flow cytometry and changes in infection driven inflammation.

8. $\alpha_1$PI augmentation therapy for neutropenia. In the majority of patients with severe congenital neutropenia, mutations are found in the gene encoding HLE or in the gene encoding the receptor for G-CSF (Horwitz et al., 1999; Benson et al., 2003). HLE mutations that prevent localization to the plasma membrane cause cyclic neutropenia, and mutations that cause exclusive localization to the plasma membrane cause the pre-leukemic disorder, severe congenital neutropenia (Benson et al., 2003). Because inactive $\alpha_1$PI mobilizes neutrophils (Joslin et al., 1992), augmentation with inactive $\alpha_1$PI is used therapeutically for the purpose of increasing the number of neutrophils in circulation. Patients receive inactive $\alpha_1$PI with a target of 39 mg/kg inactive $\alpha_1$PI and are monitored for active and inactive $\alpha_1$PI levels as well as for changes in the number of neutrophils in circulation using flow cytometry.

9. $\alpha_1$PI augmentation therapy for solid tumors. Tumor cell lines and biopsy specimens exhibit inverse correlations of $\alpha_1$PI and the metalloproteinase MMP-26 (Li et al., 2004). Expression of MMP-26 in estrogen-dependent neoplasms is likely to contribute to the inactivation of $\alpha_1$PI promoting matrix destruction and malignant progression. Furthermore, evidence suggests $\alpha_1$PI participates in tumor cell migration (Nejjari et al., 2004).

A serious side effect of myelosuppressive chemotherapy for solid tumors, is neutropenia. G-CSF (Filgrastim, Neupogen® or Neulasta®, Amgen, Inc.) is currently used to mobilize neutrophils in patients on myelosuppressive chemotherapy. In combination with G-CSF, using active $\alpha_1$PI therapeutically to mobilize lymphoid-lineage cells in patients receiving myelosuppressive chemotherapy offers the additional benefit of controlling tumor metastasis. Patients receive active $\alpha_1$PI with a target blood threshold of 35 μM active $\alpha_1$PI and are monitored for active and inactive $\alpha_1$PI levels as well as for changes in the number of myeloid-lineage, lymphoid-lineage, and tumor cells in circulation using flow cytometry.

10. $\alpha_1$PI augmentation therapy in atherosclerosis. Diminished active $\alpha_1$PI promotes atherogenesis (Talmud et al., 2003). Oxidized $\alpha_1$PI has no proteinase inhibitory activity, and instead associates with LDL in vivo (Mashiba et al., 2001). The C-terminal fragment of $\alpha_1$PI is present in atherosclerotic plaques (Dichtl et al., 2000). The oxidized and proteolyzed inactivation of $\alpha_1$PI is thought to result from subclinical infections of the arterial intima by bacteria such as Porphyromonas gingivalis (Brodala et al., 2005; Beck et al., 2005). Augmentation with active $\alpha_1$PI is used therapeutically to mobilize lymphoid-lineage cells into the infected tissue for the purpose of controlling and clearing the infection. Patients receive augmentation with active $\alpha_1$PI with a target blood threshold of 35 μM active $\alpha_1$PI and are monitored for active and inactive $\alpha_1$PI levels as well as for intimal wall thickness and atherosclerotic plaque formation.

11. $\alpha_1$PI augmentation therapy in insulin-dependent diabetes. Increased inactive $\alpha_1$PI is present in insulin-dependent diabetes due to the presence of subclinical infections (Bristow et al., 1998; Sandler et al., 1988) and hyperglycemia (Sandler et al., 1988). Recombinant adeno-associated virus-mediated $\alpha_1$PI gene therapy in a murine model reduced the level of insulin autoantibodies and the frequency of overt diabetes (Song et al., 2004). Augmentation with active $\alpha_1$PI is used therapeutically to mobilize lymphoid-lineage cells into the infected tissue for the purpose of controlling and clearing the infection as well as to ameliorate the incidence of autoantibodies in diabetes. Patients receive augmentation with active $\alpha_1$PI with a target blood threshold of 35 μM active $\alpha_1$PI and are monitored for active and inactive $\alpha_1$PI levels as well as for the presence of anti-insulin antibodies.

12. $\alpha_1$PI augmentation therapy in autoimmune diseases. A predisposing condition for the occurrence of autoimmune disease is the inborn deficiency of a proteinase or proteinase inhibitor involved in homeostasis. Wegener's granulomatosis is caused by autoimmunity to the $\alpha_1$PI ligand, proteinase 3 (Pendergraft et al., 2003; Csernok et al., 1990). Active $\alpha_1$PI ameliorates the autoimmune pathogenesis of Wegener's granulomatosis (Rooney et al., 2001). Systemic lupus erythematosis can arise in patients with complement deficiencies or $\alpha_1$PI deficiency (Sinico et al., 2005) Elevated $HLE_G$ activity is detected in patients with rheumatoid arthritis (Adeyemi et al., 1986). These patients benefit from augmentation with active $\alpha_1$PI. Patients receive augmentation with active $\alpha_1$PI with a target blood threshold of 35 μM active $\alpha_1$PI and are monitored for active and inactive $\alpha_1$PI levels as well as for autoimmune-mediated inflammation.

13. $\alpha_1$PI augmentation therapy in solid organ transplantation. Excessive activation of proteinase cascade systems has been associated with post-transplantation inflammatory disorders and organ rejection (Kirschfink, 2002). Augmentation with active $\alpha_1$PI diminishes post-transplantation inflammation; however, this therapy also mobilizes both lymphoid-lineage and myeloid-lineage cells potentially facilitating organ rejection. To overcome this adverse affect, $\alpha_1$PI is genetically modified to prevent interaction with receptors and to prevent stimulation of cell motility (see Example 5). Augmentation with genetically modified $\alpha_1$PI is used therapeutically to diminish inflammation and prevent recruitment of inflammatory blood cells and their products into transplants. Patients receive genetically modified $\alpha_1$PI with a target blood threshold of 35 μM genetically modified $\alpha_1$PI and are monitored for active and inactive $\alpha_1$PI levels as well as for markers of organ rejection.

14. $\alpha_1$PI augmentation therapy in stem cell transplantation. Migration of stem cells to, and progenitor cells from bone marrow is controlled by $HLE_{CS}$, SDF-1, CXCR4 (Tavor. S. et al., 2005; Lapidot and Petit, 2002) and $\alpha_1$PI (Examples 1-3 herein). Active $\alpha_1$PI mobilizes lymphoid-lineage cells and inactive $\alpha_1$PI mobilizes myeloid-lineage cells. Active and modified $\alpha_1$PI are used therapeutically to mobilize stem cells to hematopoietic tissue and progenitor cells from hematopoietic tissue during stem cell transplantation.

Patients undergoing stem cell transplantation are treated with G-CSF (Filgrastim, Neupogen® or Neulasta®, Amgen, Inc.) to mobilize progenitor cells into circulation, and these are primarily myeloid-committed progenitor cells (Cottler-Fox et al., 2003). Progenitor cells are harvested from blood and placed in culture in vitro for the purpose of proliferation before transplantation. Proliferation and differentiation is monitored using flow cytometry. Active $\alpha_1$PI is given therapeutically with a target blood threshold of 200 μM active $\alpha_1$PI to mobilize lymphoid-lineage cells into circulation. Mobilized lymphoid-committed progenitor cells are harvested from blood and placed in culture in vitro for the purpose of proliferation before transplantation. Patients receiving mobilization treatment with active $\alpha_1$PI are monitored for active and inactive $\alpha_1$PI levels. Harvested lymphoid-committed progenitor cells are monitored for proliferation and differentiation using flow cytometry prior to reinjection.

15. $\alpha_1$PI in producing dendritic cell-based vaccines. Autologous stem cell transplantation involves a process of harvesting stem cells from circulation, culturing the cells in vitro to proliferate, and reinjection into the patient. This same principle is used to produce autologous dendritic cell-based vaccines. Dendritic cells are used as a vector to deliver selected immunogens to the lymph nodes where their interaction with T lymphocytes initiates an immune response to the selected immunogen. Dendritic cell-based vaccines are currently being used to induce immunity to tumor antigens (Schuler et al., 2003). Monocytic or lymphocytic cells are harvested from the blood of a patient with cancer, for example, malignant melanoma. Harvested cells are cultured in vitro in the presence of a cocktail of cytokines including G-CSF and GM-CSF that induces their differentiation into either monocyte-derived dendritic cells or plasmacytoid dendritic cells depending on the combination of cytokines used (Messmer et al., 2002). Dendritic cells are loaded with an antigen, for example melanoma peptide, and reinjected into the patient (Palucka et al., 2005; Schuler et al., 2003). Patients are monitored for the presence of melanoma-specific lymphocytes.

Active $\alpha_1$PI is used to stimulate in vitro differentiation of lymphoid-lineage and myeloid-lineage blood cells into dendritic cells. Differentiation and function of dendritic cells is monitored using flow cytometry and cytokine secretion as described previously (Messmer et al., 2002). Dendritic cells are pulsed with antigen and reinjected into the patient. Patients receiving $\alpha_1$PI-induced dendritic cells are monitored for the presence of immunogen-specific lymphocytes.

REFERENCE LIST

Adeyemi, E. O., Hull, R. G., Chadwick, V. S., Hughes, G. R., and Hodgson, H. J. (1986). Circulating human leucocyte elastase in rheumatoid arthritis. Rheumatol. Int. 6, 57-60.

Ali, H., Tomhave, E. D., Richardson, R. M., Haribabu, B., and Snyderman, R. (1996). Thrombin primes responsiveness of selective chemoattractant receptors at a site distal to G protein activation. J. Biol. Chem. 271, 3200-3206.

Banda, M. J., Griffin, G. L., and Senior, R. M. (1988). α1-proteinase inhibitor is a neutrophil chemoattractant after proteolytic inactivation by macrophage elastase. J. Biol. Chem. 263, 4481-4484.

Barbey-Morel, C. and Perlmutter, D. H. (1991). Effect of *Pseudomonas elastase* on human mononuclear phagocyte $\alpha_1$antitrypsin expression. Pediatr Res 29, 133-139.

Beck, J. D., Eke, P., Lin, D., Madianos, P., Couper, D., Moss, K., Elter, J., Heiss, G., and Offenbacher, S. (2005). Associations between IgG antibody to oral organisms and carotid intima-medial thickness in community-dwelling adults. Atherosclerosis 183, 342-348.

Benson, K. F., Li, F. Q., Person, R. E., Albani, D., Duan, Z., Wechsler, J., Meade-White, K., Williams, K., Acland, G. M., Niemeyer, G., Lothrop, C. D., and Horwitz, M. (2003). Mutations associated with neutropenia in dogs and humans disrupt intracellular transport of neutrophil elastase. Nat Genet 35, 90-96.

Berninger, R. W. (1985). Alpha 1-antitrypsin. J. Med. 16, 23-99.

Bjorkman, P. J., Saper, M. A., Samraoui, B., Bennett, W. S., Strominger, J. L., and Wiley, D. C. (1987). Structure of the human class I histocompatibility antigen, HLA-A2. Nature 329, 506-512.

Brantly, M. L., Wittes, J. T., Vogelmeier, C. F., Hubbard, R. C., Fells, G. A., and Crystal, R. G. (1991). Use of a highly purified alpha 1-antitrypsin standard to establish ranges for the common normal and deficient alpha 1-antitrypsin phenotypes. Chest 100, 703-708.

Bristow, C. L. (2001). Slow human immunodeficiency virus (HIV) infectivity correlated with low HIV coreceptor levels. Clin. Diagn. Lab. Immunol. 8, 932-936.

Bristow, C. L., di Meo, F., and Arnold, R. R. (1998). Specific activity of alproteinase inhibitor and α2macroglobulin in human serum: Application to insulin-dependent diabetes mellitus. Clin. Immunol Immunopathol. 89, 247-259.

Bristow, C. L., Fiscus, S. A., Flood, P. M., and Arnold, R. R. (1995). Inhibition of HIV-1 by modification of a host membrane protease. Int. Immunol. 7, 239-249.

Bristow, C. L., Mercatante, D. R., and Kole, R. (2003). HIV-1 preferentially binds receptors co-patched with cell surface elastase. Blood 102, 4479-4486.

Bristow, C. L., Patel, H., and Arnold, R. R. (2001). Self antigen prognostic for human immunodeficiency virus disease progression. Clin Diagn. Lab. Immunol. 8, 937-942.

Brodala, N., Merricks, E. P., Bellinger, D. A., Damrongsri, D., Offenbacher, S., Beck, J., Madianos, P., Sotres, D., Chang, Y. L., Koch, G., and Nichols, T. C. (2005). Porphyromonas gingivalis Bacteremia Induces Coronary and Aortic Atherosclerosis in Normocholesterolemic and Hypercholesterolemic Pigs. Arterioscler Thromb Vasc Biol 25, 1446-1451.

Cantin, A. M. and Woods, D. E. (1999). Aerosolized Prolastin Suppresses Bacterial Proliferation in a Model of Chronic *Pseudomonas aeruginosa* Lung Infection. American Journal of Respiratory and Critical Care Medicine 160, 1130-1135.

Castro, K. G., Ward, J. W., Slutsker, L., Buehler, J. W., Jaffe, Jr. J. W., Berkelman, R. L., and Curran, J. W. (1992). 1993 revised classification system for HIV infection and expanded surveillance case definition for AIDS among adolescents and adults. Morbid. Mortal. Weekly Rep. 41, 1-19.

Cepinskas, G., Sandig, M., and Kvietys, P. R. (1999). PAF-induced elastase-dependent neutrophil transendothelial migration is associated with the mobilization of elastase to the neutrophil surface and localization to the migrating front. J. Cell Science 112, 1937-1945.

Chowanadisai, W., Huang, J., Huang, N., and Lonnerdal, B. (2003). Stability of recombinant human alpha-1-antitrypsin produced in rice in infant formula. J Nutr Biochem 14, 386-393.

Cottler-Fox, M. H., Lapidot, T., Petit, I., Kollet, O., DiPersio, J. F., Link, D., and Devine, S. (2003). Stem Cell Mobilization. Hematology 2003, 419-437.

Courtney, M., Buchwalder, A., Tessier, L.-H. J. M., Benavente, A., Balland, A., Kohli, V., Lathe, R., Tolstoshev, P., and Lecocq, J. P. (1984). High-level production of biologically active human α1—antitrypsin in *Escherichia coli*. Proc Natl Acad Sci USA 81, 669-673.

Csernok, E., Ludemann, J., Gross, W. L., and Bainton, D. F. (1990). Ultrastructural localization of proteinase 3, the target antigen of anti-cytoplasmic antibodies circulating in Wegener's granulomatosis. Am. J. Pathol. 137, 1113-1120.

Current Protocols in Molecular Biology (2002). Greene Publishing Associates and Wiley-Intersciences, New York).

Cygler, M., Rose, D. R., and Bundle, D. R. (1991). Recognition of a cell-surface oligosaccharide of pathogenic Salmonella by an antibody Fab fragment. Science 253, 442-445.

Desrochers, P. E., Mookhtiar, K., Van Wart, H. E., Hasty, K. A., and Weiss, S. J. (1992). Proteolytic inactivation of alpha 1-proteinase inhibitor and alpha 1-antichymotrypsin by oxidatively activated human neutrophil metalloproteinases. Journal of Biological Chemistry 267, 5005-5012.

Dichtl, W., Moraga, F., Ares, M. P. S., Crisby, M., Nilsson, J., Lindgren, S., and Janciauskiene, S. (2000). The Carboxyl-Terminal Fragment of [alpha]1-Antitrypsin Is Present in Atherosclerotic Plaques and Regulates Inflammatory Transcription Factors in Primary Human Monocytes. Molecular Cell Biology Research Communications 4, 50-61.

Elliott, P. R., Pei, X. Y., Dafforn, T. R., and Lomas, D. A. (2000). Topography of a 2.0 A structure of alpha1-antitrypsin reveals targets for rational drug design to prevent conformational disease [In Process Citation]. Protein Sci 9, 1274-1281.

Flotte, T. R, Brantly, M. L., Spencer, L. T., Byrne, B. J., Spencer, C. T., Baker, D. J., and Humphries, M. (2004). Phase I trial of intramuscular injection of a recombinant adeno-associated virus alpha 1-antitrypsin (rAAV2-CB-hAAT) gene vector to AAT-deficient adults. Hum Gene Ther 15, 93-128.

Garwicz, D., Lennartsson, A., Jacobsen, S. E. W., Gullberg, U., and Lindmark, A. (2005). Biosynthetic profiles of neutrophil serine proteases in a human bone marrow-derived cellular myeloid differentiation model. Haematologica 90, 38-44.

Girard, M., Mahoney, J., Wei, Q., van der Ryst, E., Muchmore, E., Barre-Sinoussi, F., and Fultz, P. N. (1998).

Genital infection of female chimpanzees with human immunodeficiency virus type 1. AIDS Res Hum Retroviruses 14, 1357-1367.

Graziadei, I., Gaggl, S., Kaserbacher, R., Braunsteiner, H., and Vogel, W. (1994). The acute-phase protein alpha 1-antitrypsin inhibits growth and proliferation of human early erythroid progenitor cells (burst-forming units-erythroid) and of human erythroleukemic cells (K562) in vitro by interfering with transferrin iron uptake. Blood 83, 260-268.

Gullberg, U., Lindmark, A., Lindgren, G., Persson, A.-M., Nilsson, E., and Olsson, I. (1995). Carboxyl-terminal prodomain-deleted human leukocyte elastase and cathepsin G are efficiently targeted to granules and enzymatically activated in the rat basophilic/mast cell line RBL. J. Biol. Chem. 270, 12912-12918.

Hooper, N. M. (2002). Proteases: a primer. Essays Biochem. 38, 1-8.

Horwitz, M., Benson, K. F., Duan, Z., Li, F. Q., and Person, R. E. (2004). Hereditary neutropenia: dogs explain human neutrophil elastase mutations, Trends Mol. Med. 10, 163-170.

Horwitz, M., Benson, K. F., Person, R. E., Aprikyan, A. G., and Dale, D. C. (1999). Mutations in ELA2, encoding neutrophil elastase, define a 21-day clock in cyclic haematopoiesis. Nat. Genet. 23, 433436.

Janciauskiene, S. and Lindgren, S. (1999). Effects of fibrillar C-terminal fragment of cleaved alpha1-antitrypsin on cholesterol homeostasis in HepG2 cells. Hepatology 29, 434-442.

Janciauskiene, S., Wright, H. T., and Lindgren, S. (1999). Atherogenic properties of human monocytes induced by the carboxyl terminal proteolytic fragment of alpha-1-antitrypsin. Atherosclerosis 147, 263-275.

Jansen, J., Hanks, S., Thompson, J. M., Dugan, M. J., and Akar, L. P. (2005). Transplantation of hematopoietic stem cells from the peripheral blood. J Cell Mol Med. 9, 37-50.

Jean, F., Stella, K., Thomas, L., Lui, G., Xiang, Y., and Reason, A. J. (1998). α1-antitrypsin Portland, a bioengineered serpin highly selective for furin: Application as an antipathogenic agent. Proc Natl Acad Sci USA 95, 7293-7298.

Jeppsson, J. O., Lilja, H., and Johansson, M. (1985). Isolation and characterization of two minor fractions of alpha 1-antitrypsin by high-performance liquid chromatographic chromatofocusing. J. Chromatogr. 327, 173-177.

Joslin, G., Fallon, R. J., Bullock, J., Adams, S. P., and Perlmutter, D. H. (1991). The SEC receptor recognizes a pentapeptide neodomain of alpha-1-antitrypsin-protease. J. Biol. Chem. 266, 11282-11288.

Joslin, G., Griffin, G. L., August, A. M., Adams, S., Fallon, R. J., Senior, R. M., and Perlmutter, D. H. (1992). The serpin-enzyme complex (SEC) receptor mediates the neutrophil chemotactic effect of α-$_1$antitrypsin-elastase complexes and amyloid-β peptide. J. Clin. Invest. 90, 1150-1154.

Kindzelskii, A. L. and Petty, H. R. (2003). Intracellular Calcium Waves Accompany Neutrophil Polarization, Formylmethionylleucylphenylalanine Stimulation, and Phagocytosis: A High Speed Microscopy Study. J. Immunol. 170, 64-72.

Kirschfink, M. (2002). C1-inhibitor and transplantation. Immunobiology 205, 534-541.

Kounnas, M. Z., Church, F. C., Argraves, W. S., and Strickland, D. K. (1996). Cellular internalization and degradation of antithrombin III-thrombin, heparin cofactor III-thrombin, and alpha 1-antitrypsin-trypsin complexes is mediated by the low density lipoprotein receptor-related protein. J. Biol. Chem. 271, 6523-6529.

Kushner, I. (1982). The phenomenon of the acute phase response. Ann. N. Y. Acad. Sci. 389, 39-47.

Lapidot, T. and Petit, I. (2002). Current understanding of stem cell mobilization: The roles of chemokines, proteolytic enzymes, adhesion molecules, cytokines, and stromal cells. Exp. Hematol. 30, 973-981.

Leonard, C. K., Spellman, M. W., Riddle, L., Harris, R. J., Thomas, J. N., and Gregory, T. J. (1987). Assignment of intrachain disulfide bonds and characterization of potential glycosylation. J. Biol. Chem. 265, 10373-10382.

Li, W., Savinov, A. Y., Rozanov, D. V., Golubkov, V. S., Hedayat, H., Postnova, T. I., Golubkova, N. V., Linli, Y., Krajewski, S., and Strongin, A. Y. (2004). Matrix Metalloproteinase-26 Is Associated with Estrogen-Dependent Malignancies and Targets { alpha}1-Antitrypsin Serpin. Cancer Res 64, 8657-8665.

Luisetti, M. and Travis, J. (1996). Bioengineering: alpha 1-antiproteinase inhibitor site-specific mutagenesis. The prospect for improving the inhibitor. Chest 110, 278-283.

Marinaki, S., Neumann, I., Kalsch, A. I., Grimminger, P., Breedijk, A., Birck, R., Schmitt, W., Waldherr, R., Yard, B. A., and van der Woude, F. J. (2005). Abnormalities of CD4+ T cell subpopulations in ANCA-associated vasculitis. Clinical and Experimental Immunology 140, 181-191.

Mashiba, S., Wada, Y., Takeya, M., Sugiyama, A., Hamakubo, T., Nakamura, A., Noguchi, N., Niki, E., Izumi, A., Kobayashi, M., Uchida, K., and Kodama, T. (2001). In Vivo Complex Formation of Oxidized {alpha}1-Antitrypsin and LDL. Arterioscler Thromb Vasc Biol 21, 1801-1808.

Mast, A. E., Enghild, J. J., Nagase, H., Suzuki, K., Pizzo, S. V., and Salvesen, G. (1991). Kinetics and physiologic relevance of the inactivation of alpha 1-proteinase inhibitor, alpha 1-antichymotrypsin, and antithrombin III by matrix metalloproteinases-1 (tissue collagenase), -2 (72-kDa gelatinase/type IV collagenase), and -3 (stromelysin). Journal of Biological Chemistry 266, 15810-15816.

Mellet, P., Boudier, C., Mely, Y., and Bieth, J. G. (1998). Stopped Flow Fluorescence Energy Transfer Measurement of the Rate Constants Describing the Reversible Formation and the Irreversible Rearrangement of the Elastase-alpha 1-Proteinase Inhibitor Complex. Journal of Biological Chemistry 273, 9119-9123.

Messmer, D., Jacque, J.-M., Santisteban, C., Bristow, C. L., Han, S.-Y., Villamide-Herrera, L., Mehlhop, E. R., Marx, P. A., Steinman, R. M., Gettie, A., and Pope, M. (2002). Endogenously expressed nef uncouples cytokine and chemokine production from membrane phenotypic maturation in dendritic cells. J. Immunol. 169, 4172-4182.

Methods in Enzymology. Proteolytic Enzymes. Perlmann, G. E. and Lorand, L. [19]. 1970. Acaemic Press. Colowick, S. P. and Kaplan, N. O.
Ref Type: Serial (Book, Monograph)

Moore, J. P., Sattentau, Q. E., Wyatt, R., and Sodroski, J. (1994). Probing the structure of the human immunodeficiency virus surface glycoprotein gp120 with a panel of monoclonal antibodies. J. Virol. 68, 469-484.

Nejjari, M., Berthet, V., Rigot, V., Laforest, S., Jacquier, M. F., Seidah, N. G., Remy, L., Bruyneel, E., Scoazec, J. Y., Marvaldi, J., and Luis, J. (2004). Inhibition of Proprotein Convertases Enhances Cell Migration and Metastases Development of Human Colon Carcinoma Cells in a Rat Model. Am J Pathol 164, 1925-1933.

Nukiwa, T., Satoh, K., Brantly, M. L., Ogushi, F., Fells, G. A., Courtney, M., and Crystal, R. G. (1986). Identification of a second mutation in the protein-coding sequence of the Z type alpha 1-antitrypsin gene. J. Biol. Chem. 261, 15989-15994.

OMIM. Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.). 2000.

Ref Type: Data File

Palucka, A. K., Dhodapkar, M. V., Paczesny, S., Ueno, H., Fay, J., and Banchereau, J. (2005). Boosting vaccinations with peptide-pulsed CD34+ progenitor-derived dendritic cells can expand long-lived melanoma peptide-specific CD8+ T cells in patients with metastatic melanoma. J Immunother. 28, 158-168.

Parfrey, H., Mahadeva, R., Ravenhill, N. A., Zhou, A., Dafforn, T. R., Foreman, R. C., and Lomas, D. A. (2003). Targeting a surface cavity of $\alpha_{1\text{-antitrypsin to prevent conformational disease}}$. J. Biol. Chem. 278, 33060-33066.

Pei, D., Majmudar, G., and Weiss, S. J. (1994). Hydrolytic inactivation of a breast carcinoma cell-derived serpin by human stromelysin-3. J. Biol. Chem. 269, 25849-25855.

Pendergraft, W. F., Preston, G. A., Shah, R. R., Tropsha, A., Carter, C. W., Jennette, J. C., and Falk, R. J. (2003). Autoimmunity is triggered by cPR-3(105-201), a protein complementary to human autoantigen proteinase-3. Nat Med. 10 Epub 2003 Dec. 7., 72-79.

Percherancier, Y., Berchiche, Y., Slight, I., Volkmer-Engert, R., Tamamura, H., Fujii, N., Bouvier, M., and Heveker, N. (2005). Bioluminescence resonance energy transfer reveals ligand-induced conformational changes in CXCR4 homo- and heterodimers. Journal of Biological Chemistry M411151200.

Perkins, S. J., Smith, K. F., Nealis, A. S., Haris, P. I., Chapman, D., Bauer, C. J, and Harrison, R. A. (1992). Secondary structure changes stabilize the reactive-centre cleaved form of SERPINs. J. Mol. Biol. 228, 1235-1254.

Person, R. E., Li, F.-Q., Duan, Z., Benson, K, F., Wechsler, J., Papadaki, H. A., Eliopoulos, G., Kaufman, C., Bertolone, S. J., Nakamoto, B., Papayannopoulou, T., Grimes, H. L., and Horwitz, M. (2003). Mutations in proto-oncogene GFII cause human neutropenia and target ELA2. Nature Genetics 34, 308-312.

Petit, I., Szyper-Kravitz, M., Nagler, A., Lahav, M., Peled, A., Habler, L., Ponomaryov, T., Taichman, R. S., Arenzana-Seisdedos, F., Sandbank, J., Zipori, D., and Lapidot, T. (2002). G-CSF induces stem cell mobilization by decreasing bone marrow SDF-1 and up-regulating CXCR4. Nature Immunol 3, 687-694.

Poller, W., Willnow, T. E., Hilpert, J., and Herz, J. (1995). Differential recognition of alpha 1-antitrypsin-elastase and alpha 1-antichymotrypsin-cathepsin-G complexes by the low density lipoprotein receptor-related protein. J. Biol. Chem. 270, 2841-2845.

Pratt, C. W., Roche, P. A., and Pizzo, S. V. (1987). The role of inter-a-trypsin inhibitor and other proteinase inhibitors in the plasma clearance of neutrophil elastase and plasmin Arch. Biochem. Biophys. 258, 591-599.

Ratner, L., Haseltine, W., Patarca, R., Livak, K. J., Starcich, B., Joseph, S. F., Doran, E. R., Rafalski, J. A., Whitehorn, E. A., Baumeister, K., and et al. (1985). Complete nucleotide sequence of the AIDS virus, HTLV-III. Nature 313, 277-284.

Rooney, C. P., Taggart, C., Coakley, R., McElvaney, N. G., and O'Neill, S. J. (2001). Anti-Proteinase 3 Antibody Activation of Neutrophils Can Be Inhibited by alpha 1-Antitrypsin. American Journal of Respiratory Cell and Molecular Biology 24, 747-754.

Rutjens, E. B.-J. S., Verschoor, E., Bogers, W., Koopman, G., and Heeney, J. (2003). Lentivirus infections and mechanisms of disease resistance in chimpanzees. Front. Biosci. 8, d1134-1145.

Sandler, M., Gemperli, B. M., Hanekom, C., and Kuhn, S. H. (1988). Serum $\alpha_1$-protease inhibitor in diabetes mellitus: reduced concentration and impaired activity. Diabetes Res Clin Pract 5, 249-255.

Sandoval, C., Stojanova, A., DiFalco, M. R., and Congote, L. F. (2003). The fusion of IGFI with stromal cell-derived factor I or [alpha]1 proteinase inhibitor alters their mitogenic or chemotactic activities while keeping their ability to inhibit HIV-1-gp120 binding. Biochemical Pharmacology 65, 2055-2063.

Schuler, G., Schuler-Thurner, B., and Steinman, R. M. (2003). The use of dendritic cells in cancer immunotherapy. Current Opinion in Immunology 15, 138-147.

Sifers, R. N., Brashears-Macatee, S., Kidd, V. J., Muensch, H., and Woo, S. L. (1988). A frameshift mutation results in a truncated alpha 1-antitrypsin that is retained within the rough endoplasmic reticulum. Journal of Biological Chemistry 263, 7330-7335.

Sinico, R. A., Radice, A. N. T. O., kehata, M. A. S. A., iammerresi, G. A. I. A., orace, C. A. T. E., rrigo, G. I. R. O., ollini, B. R. U. N., i Vecchi, M. A. U. R., and Iacomini, J. (2005). Anti-Clq Autoantibodies in Lupus Nephritis: Prevalence and Clinical Significance. Ann NY Acad Sci 1050, 193-200.

Song, G., Goudy, K., Campbell-Thompson, M., Wasserfall, C., Scott-Jorgensen, M., Wang, J., Tang, Q., Crawford, J. M., Ellis, T. M., Atkinson, M. A., and Flotte, T. R (2004). Recombinant adeno-associated virus-mediated alpha-1 antitrypsin gene therapy prevents type I diabetes in NOD mice. Gene Ther 11, 181-186.

Talmud, P. J., Martin, S., Steiner, G., Flavell, D. M., Whitehouse, D. B., Nagl, S., Jackson, R., Taskdnen, M. R., Frick, M. H., Nieminen, M. S., Kesaniemi, Y. A., Pasternack, A., Humphries, S. E., Syvanne, M., and the Diabetes Atherosclerosis Intervention Study Investigators (2003). Progression of Atherosclerosis Is Associated With Variation in the {alpha}1-Antitrypsin Gene. Arterioscler Thromb Vasc Biol 23, 644-649.

Tavor. S., Petit, I., Porozov, S., Goichberg, P., Avigdor, A., Sagiv, S., Nagler, A., Naparstek, E., and Lapidot, T. (2005). Motility, proliferation and egress to the circulation of human AML cells in transplanted NOD/SCID mice are elastase dependent. Blood 106, 2120-2127.

Terashima, M., Murai, T., Kawamura, M., Nakanishi, S., Stoltz, T., Chen, L., Drohan, W., Rodriguez, R. L., and Katoh, S. (1999). Production of functional human α1-antitrypsin by plant cell culture. Appl Microbiol Biotechnol 52, 516-523.

Virella, G., Wohltmann, H., Sagel, J., Lopes-Virella, M. F. L., Kilpatrick, M., Phillips, C. B., and Colwell, J. (1981). Soluble immune complexes in patients with Diabetes Mellitus: Detection and pathological significance. Diabetologia 21, 184-191.

Weaver, A. M., Hussaini, I. M., Mazar, A., Henkin, J., and Gonias, S. L. (1997). Embryonic Fibroblasts That Are Genetically Deficient in Low Density Lipoprotein Receptor-related Protein Demonstrate Increased Activity of the Urokinase Receptor System and Accelerated Migration on Vitronectin. Journal of Biological Chemistry 272, 14372-14379.

Wei, X., Decker, J. M., Wang, S., Hui, H., Kappes, J. C., Wu, X., Salazar-Gonzalez, J. F., Salazar, M. G., Kilby, J. M., Saag, M. S Komarova, N. L., Nowak, M. A., Hahn, B. H., Kwong, P. D., and Shaw, G. M. (2003). Antibody neutralization and escape by HIV-1. Nature 422, 307-312.

Winkler, I. G., Hendy, J., Coughlin, P., Horvath, A., and Levesque, J. P. (2005). Serine protease inhibitors serpina1 and serpina3 are down-regulated in bone marrow during hematopoietic progenitor mobilization. The Journal of Experimental Medicine 201, 1077-1088.

Wolf, K., Muller, R., Borgmann, S., Brocker, E. B., and Friedl, P. (2003). Amoeboid shape change and contact guidance: T-lymphocyte crawling through fibrilar collagen is independent of matrix remodeling by MMPs and other proteases. Blood 102, 3262-3269.

Wright, S. D. and Meyer, B. C. (1986). Phorbol esters cause sequential activation and deactivation of complement receptors on polymorphonuclear leukocytes. J. Immunol. 136, 1759-1764.

The present invention is not to be limited in scope by the specific embodiments described herein. Indeed, various modifications of the invention in addition to those described herein will be apparent to those skilled in the art from the foregoing description and the accompanying figures.

Patents, patent applications, publications, product descriptions, and protocols are cited throughout this application, the disclosures of which are incorporated herein by reference in their entireties for all purposes.

What is claimed is:

1. A method for increasing the number of circulating CD4+ lymphocytes in an HIV-1-infected human subject having less than 500 HIV-1 RNA copies per ml and receiving antiretroviral therapy comprising administering to a subject in need of such treatment a pharmaceutical composition comprising an amount of an active α1 proteinase inhibitor (α1PI) consisting of the amino acid sequence as set forth in SEQ ID NO: 3 effective to increase the number of circulating CD4+ lymphocytes in said subject.

2. The method of claim 1 further comprising administering a pharmaceutically acceptable carrier or excipient.

3. The method of claim 1 wherein said effective amount is 60 mg/kg per week.

4. The method of claim 3 further comprising monitoring said patients for changes in complete blood count, differential and CD4+ T-cells using flow cytometry.

5. A method for increasing the number of CD4+ T-cells in a subject infected with HIV-1 having less than 500 copies HIV-1 RNA per ml and receiving antiretroviral therapy comprising administering to a subject in need of such treatment a pharmaceutical composition comprising an amount of an active al proteinase inhibitor ($\alpha$1PI) consisting of the amino acid sequence as set forth in SEQ ID NO: 3 effective to increase the number of said CD4+ T-cells in said subject.

6. The method of claim 5 further comprising administering a pharmaceutically acceptable carrier or excipient.

7. The method of claim 6 wherein said effective amount is 60 mg/kg per week.

8. The method of claim 7 further comprising monitoring said patients for changes in complete blood count, differential and CD4+ T-cells using flow cytometry.

* * * * *